(12) United States Patent
Healy et al.

(10) Patent No.: US 10,995,225 B2
(45) Date of Patent: May 4, 2021

(54) MACROCYCLIC POLYPHENOLS FOR UNIVERSAL COATINGS

(71) Applicant: The Regents of the University of California, Oakland, CA (US)

(72) Inventors: Kevin Healy, Moraga, CA (US); Phillip B. Messersmith, Kensington, CA (US); Willie Mae Reese, Oakland, CA (US); Patrick Burch, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 80 days.

(21) Appl. No.: 16/078,493

(22) PCT Filed: Feb. 22, 2017

(86) PCT No.: PCT/US2017/018867
§ 371 (c)(1),
(2) Date: Aug. 21, 2018

(87) PCT Pub. No.: WO2017/147145
PCT Pub. Date: Aug. 31, 2017

(65) Prior Publication Data
US 2019/0085185 A1 Mar. 21, 2019

Related U.S. Application Data

(60) Provisional application No. 62/298,546, filed on Feb. 23, 2016, provisional application No. 62/299,415, filed on Feb. 24, 2016.

(51) Int. Cl.
*C09D 7/65* (2018.01)
*C09D 5/00* (2006.01)
(Continued)

(52) U.S. Cl.
CPC ............. *C09D 7/65* (2018.01); *B01L 3/5027* (2013.01); *C07C 39/15* (2013.01); *C07C 39/23* (2013.01);
(Continued)

(58) Field of Classification Search
CPC .. C09D 7/65; C09D 5/00; C07C 39/15; C07C 39/23; C07C 217/94; C07C 245/20;
(Continued)

(56) References Cited

U.S. PATENT DOCUMENTS

| 2009/0269380 A1 | 10/2009 | Baker, Jr. et al. |
| 2014/0364391 A1 | 12/2014 | Hai et al. |
| 2015/0064455 A1 | 3/2015 | Jabin et al. |

FOREIGN PATENT DOCUMENTS

| EP | 0 954 965 A1 | 4/1999 |
| WO | 2015/066171 A1 | 5/2015 |

OTHER PUBLICATIONS

Thomas, Shane, International Search Report and Written Opinion, PCT/US2017/018867, United States Patent and Trademark Office, dated May 19, 2017.
(Continued)

*Primary Examiner* — Shane Fang
(74) *Attorney, Agent, or Firm* — Gavrilovich, Dodd & Lindsey LLP

(57) ABSTRACT

The disclosure provides for coating compositions comprising macrocycles and salts in aqueous buffer and the use of the coating composition to prevent absorption of small molecules into polymeric surfaces.

14 Claims, 16 Drawing Sheets

(51) Int. Cl.
  *C07C 245/20*  (2006.01)
  *C07C 217/94*  (2006.01)
  *C07C 39/23*  (2006.01)
  *B01L 3/00*  (2006.01)
  *C07C 39/15*  (2006.01)

(52) U.S. Cl.
  CPC .......... *C07C 217/94* (2013.01); *C07C 245/20* (2013.01); *C09D 5/00* (2013.01); *B01L 2300/16* (2013.01); *C07C 2601/16* (2017.05); *C07C 2603/52* (2017.05); *C07C 2603/54* (2017.05)

(58) Field of Classification Search
  CPC ............ C07C 2603/54; C07C 2603/52; C07C 2601/16; B01L 2300/16
  USPC ........................................................ 528/397
  See application file for complete search history.

(56) References Cited

OTHER PUBLICATIONS

Baharlou, Simin, International Preliminary Report on Patentability and Written Opinion, PCT/US2017/018867, United States Patent and Trademark Office, dated Sep. 7, 2018.

| Arene | HS-MS | HPLC | NMR | Known | in accordance? | Single Crystals |
|---|---|---|---|---|---|---|
| PG-Y | good | 1 Peak | clear | $^1$H | Yes | Known |
| PG-M | good | unclear | clear | $^1$H | Yes | Known |
| PG-D | good | 2 Peaks | clean | No | | grown |
| D-M | not found | 2 Peaks | clean | No | | grown |
| D-D | good | 2 Peaks | clean | No | | Not grown yet |

Optimized Conditions:
1mg/mL D-D, 0.5 M MgCl$_2$, pH 8.5,
0.2 M Bicine buffer, r.t., o.n.

Dime:
Cu Core, Ni Shell
Penny:
Zn Core, Cu Shell

MACROCYCLIC POLYPHENOLS FOR UNIVERSAL COATINGS

CROSS REFERENCE TO RELATED APPLICATIONS

This application claims priority under 35 U.S.C. § 119 from U.S. Provisional Application Ser. No. 62/298,546, filed Feb. 23, 2016 and U.S. Provisional Application Ser. No. 62/299,415, filed Feb. 24, 2016, the disclosures of which are incorporated herein by reference.

STATEMENT OF GOVERNMENT SUPPORT

This application is a U.S. National Stage Application filed under 35 U.S.C. § 371 and claims priority from International Application No. PCT/US2017/018867, filed Feb. 22, 2017, which application claims priority under 35 U.S.C. § 119 from U.S. Provisional Application Ser. No. 62/298,546, filed Feb. 23, 2016 and U.S. Provisional Application Ser. No. 62/299,415, filed Feb. 24, 2016, the disclosures of which are incorporated herein by reference.

TECHNICAL FIELD

The disclosure provides for coating compositions comprising macrocycles and salts in aqueous buffer and the use of the coating composition to prevent absorption of small molecules into polymeric surfaces.

BACKGROUND

Drug development is a painstaking process with an estimated price tag of $2.6 billion for a single compound. The most time expensive stages of the drug development process occur in the early and late discovery periods, and the most cost taxing stages occur in the preclinical and clinical trials. Nearly 40% of drugs that make it to preclinical trials fail, and 89% of drugs that make it to clinical trials fail resulting in a great loss of resources and time. New models and methods are needed to increase the predictive power of in vitro testing to reduce the number of false positive and false negative candidates. However, such models and system often times have their own independent issues absorption and cross-reactivities.

SUMMARY

The disclosure provides for coating compositions comprising macrocycles (e.g., polyphenolic macrocycles) and salts in an aqueous buffer. The coating compositions of the disclosure are very beneficial for preventing drug absorbance into polymers used in drug screening devices. A simple dip-coating procedure can be utilized with countess substrates (e.g., polymeric materials) to form universal protective coatings. The coatings provided by the coating compositions of the disclosure outperformed existing dip-coating precursor molecules such as pyrogallol or dopamine in their ability to prevent absorbance of small molecules into a variety of organic and inorganic polymers, such as poly (dimethyl siloxane) (PDMS).

In a particular embodiment, the disclosure provides for a coating composition comprising one or more salts and one or more macrocycles in an aqueous buffer, wherein the one or more macrocycles comprise the structure of Formula I:

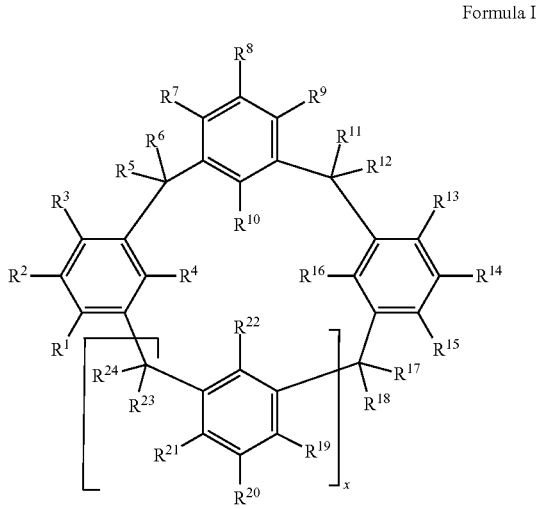

Formula I wherein, $R^1$-$R^{24}$ are independently selected from the group consisting of H, optionally substituted $(C_1$-$C_6)$alkyl, hydroxyl, halo, $(C_1$-$C_5)$alkoxy, aldehyde, carbonyl, carboxyl, ester; and x is an integer selected from 1, 2, 3, and 4, or a range including any two of the foregoing integers. In a further embodiment, a coating composition disclosed herein comprises one or more macrocycles having the structure of Formula I(a):

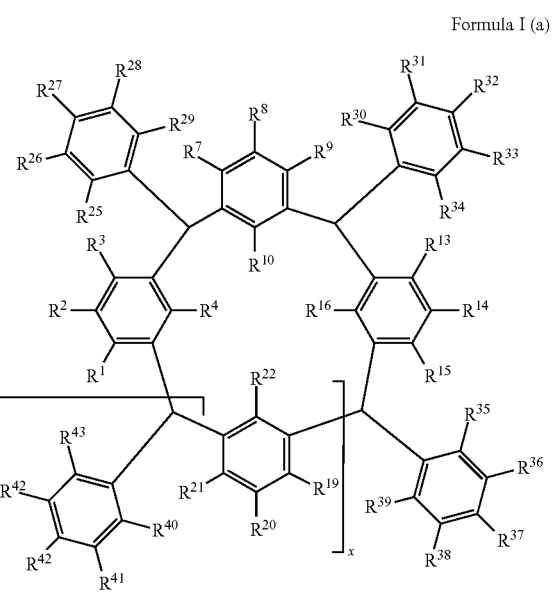

Formula I(a)

wherein, $R^1$-$R^4$, $R^7$-$R^{10}$, $R^{13}$-$R^{16}$, $R^{19}$-$R^{22}$, and $R^{25}$-$R^{43}$ are independently selected from the group consisting of H, optionally substituted $(C_1$-$C_6)$alkyl, hydroxyl, halo, $(C_1$-$C_5)$ alkoxy, aldehyde, carbonyl, carboxyl, ester; and x is an integer selected from 1, 2, 3, 4, or a range including any two of the foregoing integers. In yet a further embodiment, a coating composition disclosed herein comprises one or more macrocycle having a structure of any one of the following:

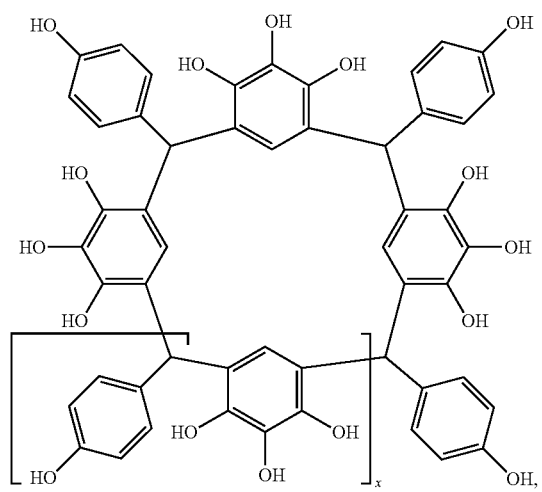

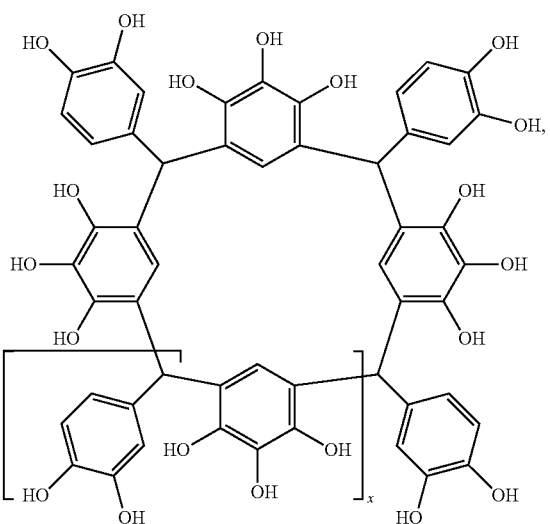

and/or

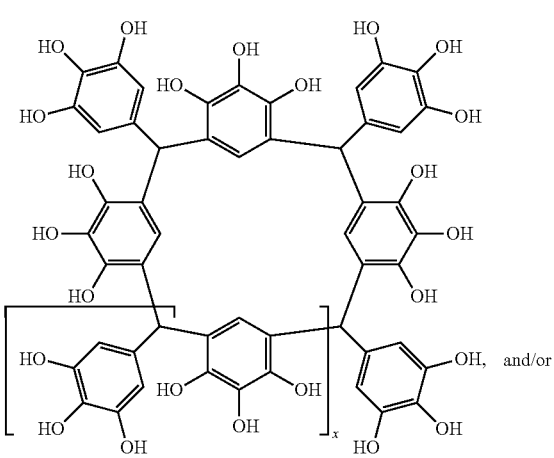

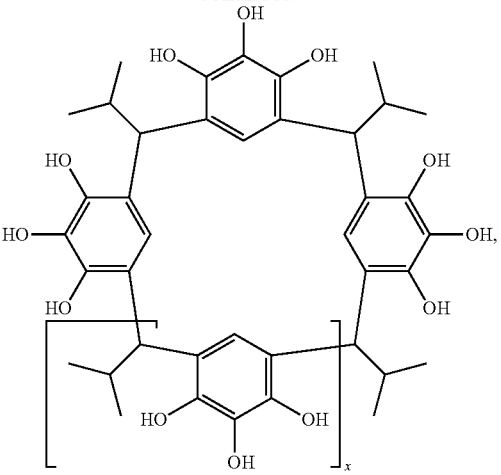

wherein, x is an integer selected from 1, 2, 3, 4, or a range including any two of the foregoing integers. In another embodiment, a coating composition disclosed herein comprises between 0.5 mg/mL and 5 mg/mL of one or more macrocycles of the disclosure. In yet another embodiment, a coating composition of the disclosure comprises 1 mg/mL of one or more macrocycles disclosed herein. In a further embodiment, a macrocycle disclosed herein is dissolved in a polar aprotic solvent. In a certain embodiment, a coating composition disclosed herein comprises one or more salts selected from NaCl, $CaCl_2$, $MgCl_2$, $CuCl_2$, $FeCl_2$, or a mixture of any of the foregoing. In a further embodiment, a coating composition of the disclosure comprises $MgCl_2$ or $CaCl_2$. In yet a further embodiment, a coating composition disclosed herein comprises one or more salts at a concentration of 0.1M to 3.0M. In yet a further embodiment, a coating composition disclosed herein comprises a buffered aqueous solution selected from phosphate buffered saline, tris-buffered saline, bicine, tricine, glycinamide, 3-[[1,3-dihydroxy-2-(hydroxymethyl)propan-2-yl]amino]propane-1-sulfonic acid (TAPS), 3-[4-(2-hydroxyethyl)piperazin-1-yl]propane-1-sulfonic acid (HEPPS), N-(2-Hydroxyethyl)-piperazine-N'-2-hydroxypropanesulfonic acid (HEPPSO), iperazine-1,4-bis(2-hydroxypropanesulfonic acid) dihydrate, Piperazine-N,N'-bis(2-hydroxypropanesulfonic acid) (POPSO), 3-[[1,3-dihydroxy-2-(hydroxymethyl)propan-2-yl]amino]-2-hydroxypropane-1-sulfonic acid (TAPSO), 3-(N,N-Bis[2-hydroxyethyl]amino)-2-hydroxypropane-sulfonic acid (DIPSO), (4-(2-hydroxyethyl)-1-piperazineethanesulfonic acid) (HEPES), 2-[[1,3-dihydroxy-2-(hydroxymethyl)propan-2-yl]amino]ethanesulfonic acid (TES), N,N-Bis(2-hydroxyethyl)-2-aminoethanesulfonic acid, N,N-Bis(2-hydroxyethyl)taurine (BES), (3-(N-morpholino)propanesulfonic acid) (MOPS), 3-morpholino-2-hydroxypropanesulfonic acid (MOPSO), piperazine-N,N'-bis(2-ethanesulfonic acid) (PIPES), gly buffer, or a mixture of any of the foregoing. In yet another embodiment, a coating composition of disclosure comprises a bicine aqueous buffer. In a certain embodiment, the disclosure provides for a coating composition disclosed herein comprising an aqueous buffer that has a pH from 7 to 10.

In a particular embodiment, the disclosure also provides for a method of coating one or more surfaces of a substrate comprising coating the substrate with the coating composition disclosed herein. In a further embodiment, the one or more surfaces of a substrate is coated using dip coating or spin coating. In yet a further embodiment, the one or more surfaces that are coated comprises a polymer material, e.g., a synthetic polymer material, a natural polymer material, an organic polymer material, or an inorganic polymer material. In a certain embodiment, the disclose provides for coating a surface comprising poly(dimethyl siloxane) (PDMS) with a coating composition disclosed herein. In another embodiment, the disclosure provides for coating one of more surfaces that of a microfluidic or microphysiological system (MPS) with a coating composition disclosed herein.

In a particular embodiment, the disclosure provides for a microfluidic or MPS comprising one or more surfaces coated with the coating composition disclosed herein. In a further embodiment, the microfluidic or MPS comprises PDMS.

DESCRIPTION OF DRAWINGS

FIG. 10 displays the results of a stability screen comprising the D-D macrocycle and 0.5 M $MgCl_2$ in Bicine buffer using the indicated conditions. The stability experiments were run overnight at room temperature or at 36° C. for PBS.

FIG. 11 presents the results of coating various synthetic polymers with the coating compositions of the disclosure.

As shown, the coatings were relatively stable on all substrates when incubated overnight in PBS at 36° C. PC=polycarbonate, PEEK=polyether ether ketone, PS=polystyrene, PPS=polyphenylene sulfide, PTFE=poltetrafluoroethylene, CC=cell culture, and PDMS=polydimethylsilane.

Figure 12:
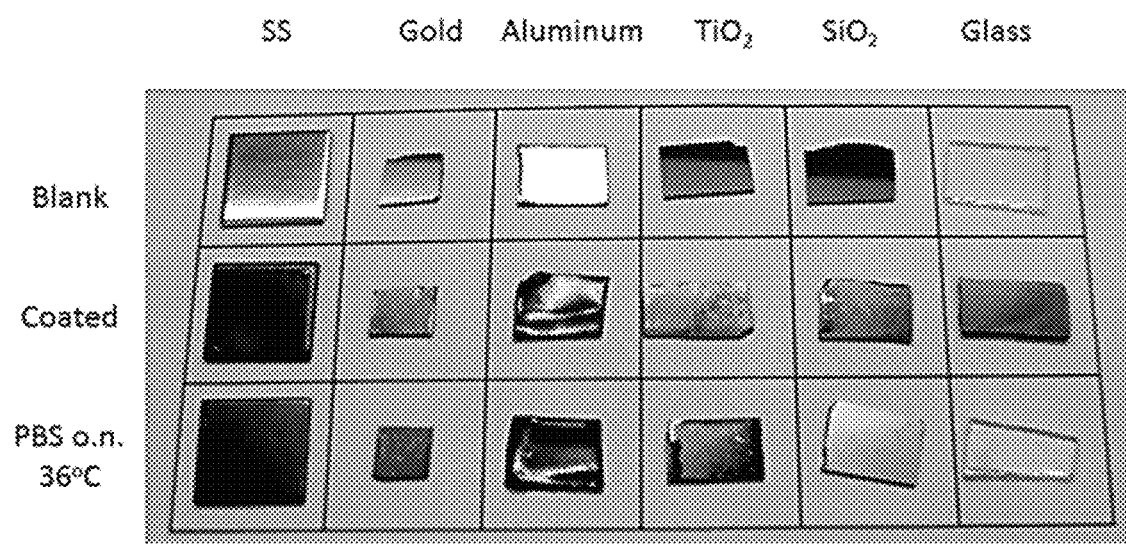

FIG. 12 shows the results of coating various metals with the coating compositions of the disclosure. SS=stainless steel.

Figure 13:
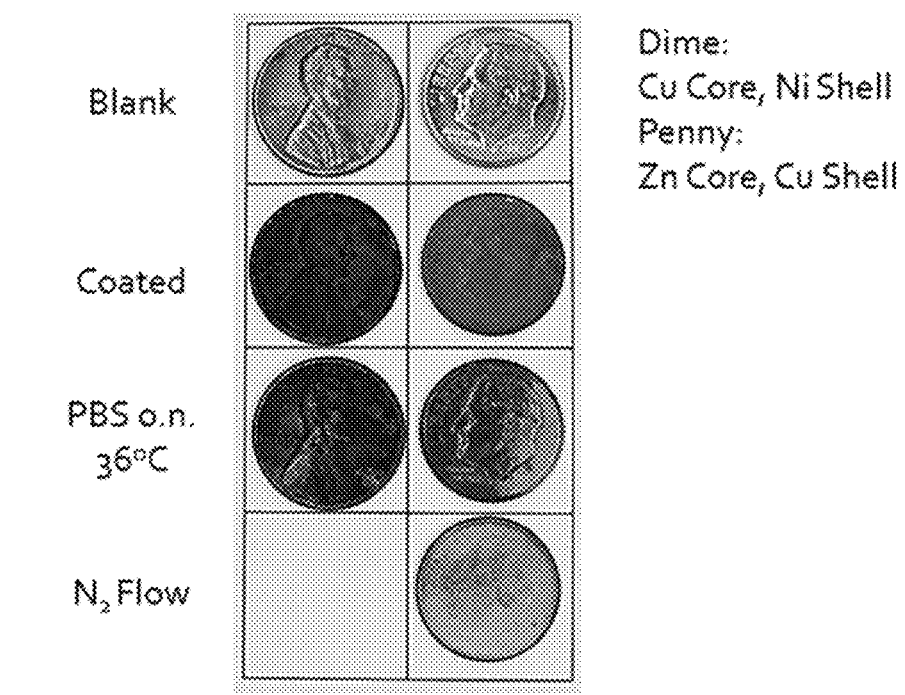

FIG. 13 presents the results of coating coins using the coating compositions of the disclosure.

Figure 14:
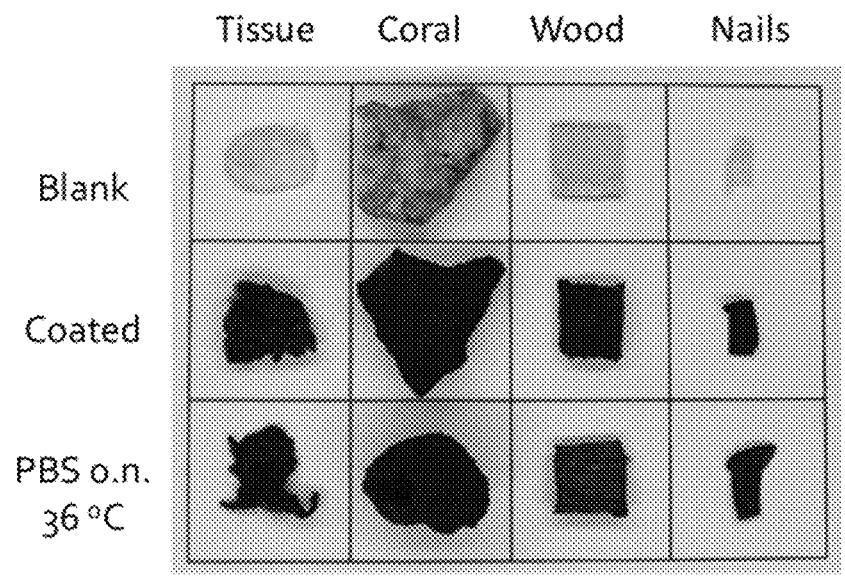

FIG. 14 displays the results of coating natural substances using the coating compositions of the disclosure.

Figure 15:
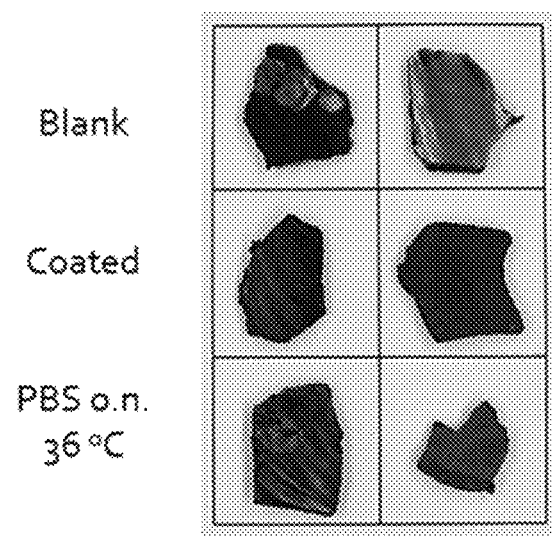

FIG. 15 presents the results of coating a mussel shell using the coating compositions of the disclosure.

Figure 16:
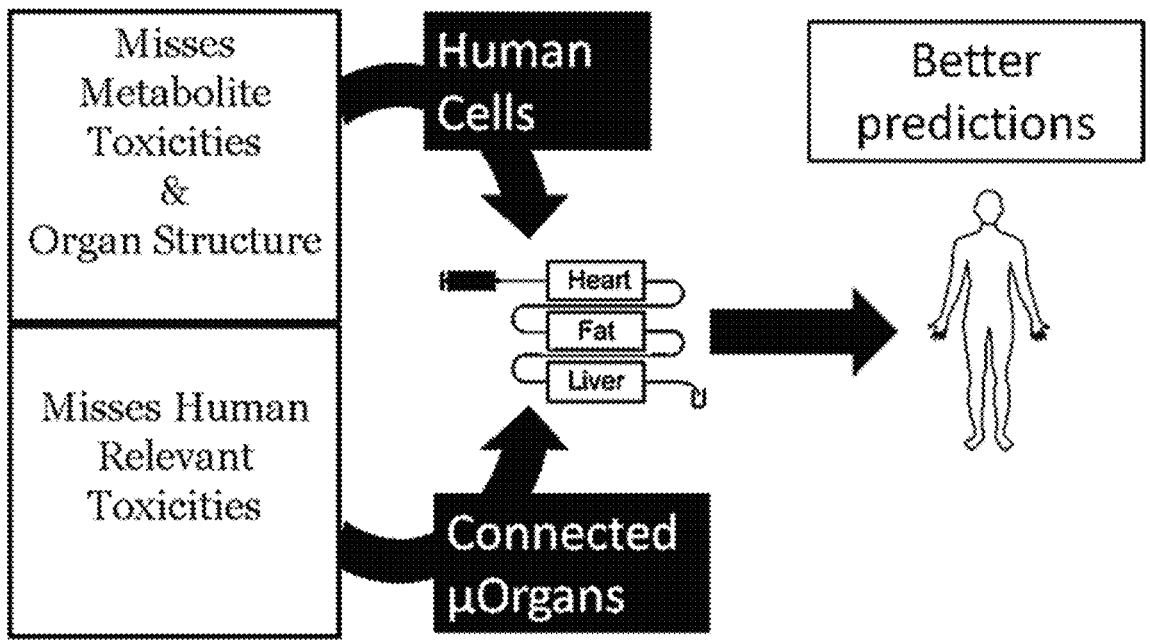

FIG. 16 provides a cartoon showing that most drugs fail clinical trials and that the in vitro systems used to first test the drugs does not reliably predict efficacy in human subjects.

Figure 17A:
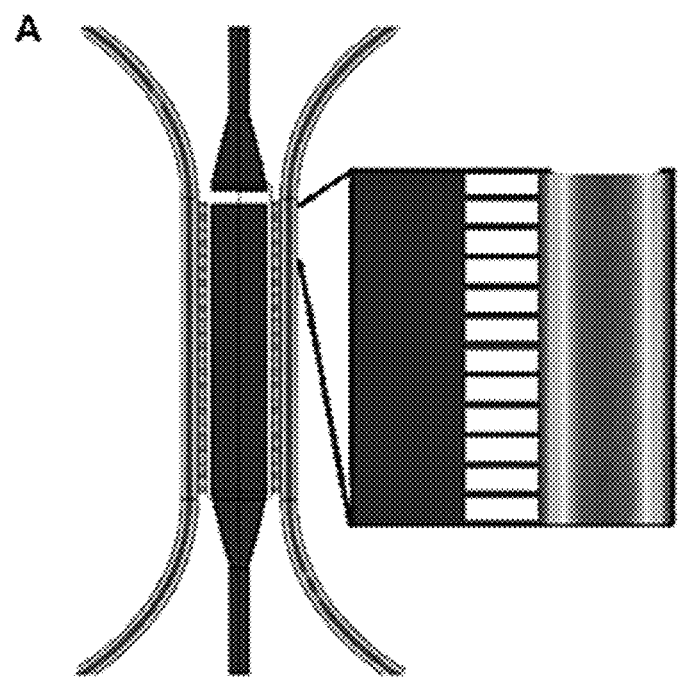
Figure 17B:
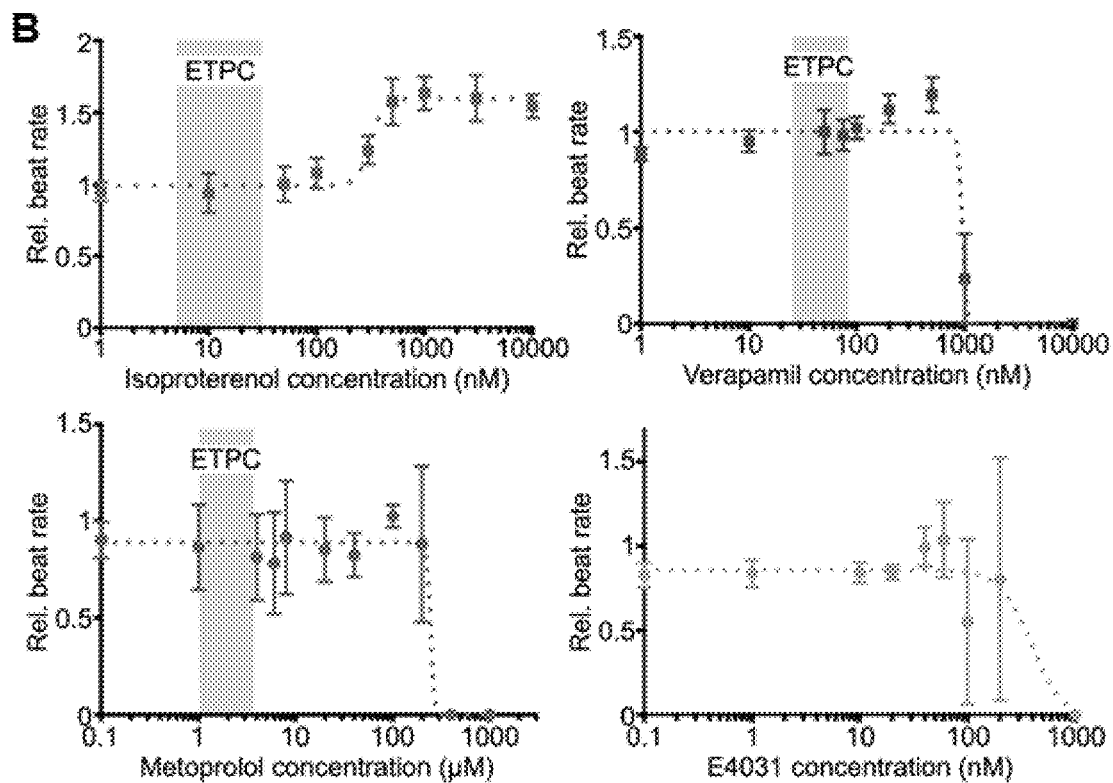
Figure 17C:
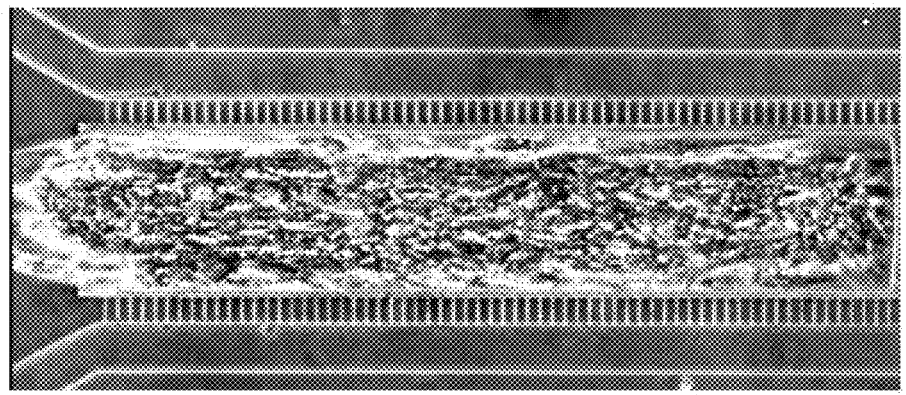

FIG. 17A-C displays a human iPSC-based cardiac microphysiological system for drug screening applications. (A) presents a schematic diagram of the microphysiological system (MPS); (B) results of screens using the device with various drugs; and (C) a micrograph of the system comprising human iPSC.

Figure 18A:
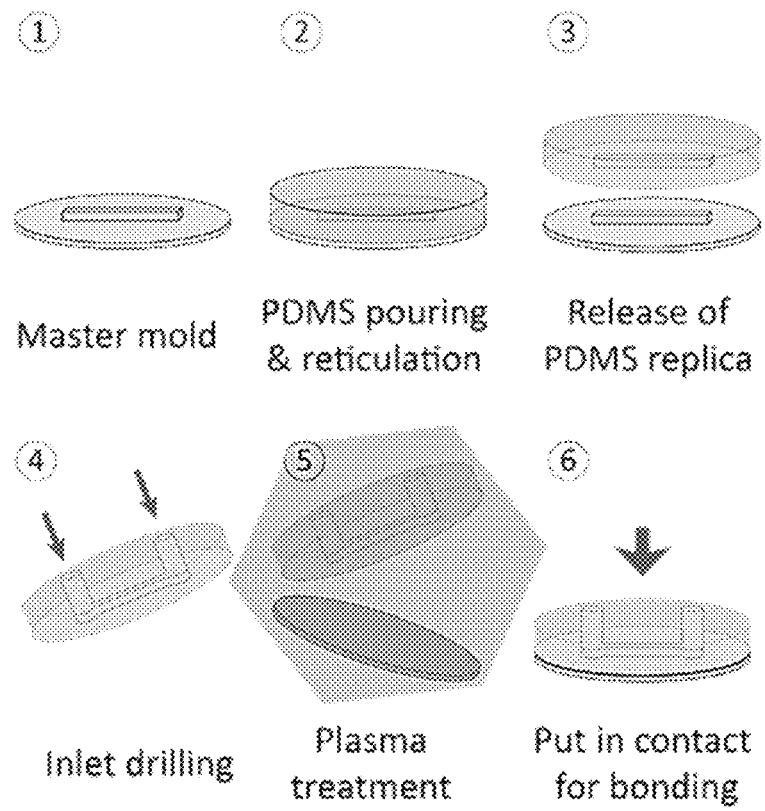
Figure 18B:
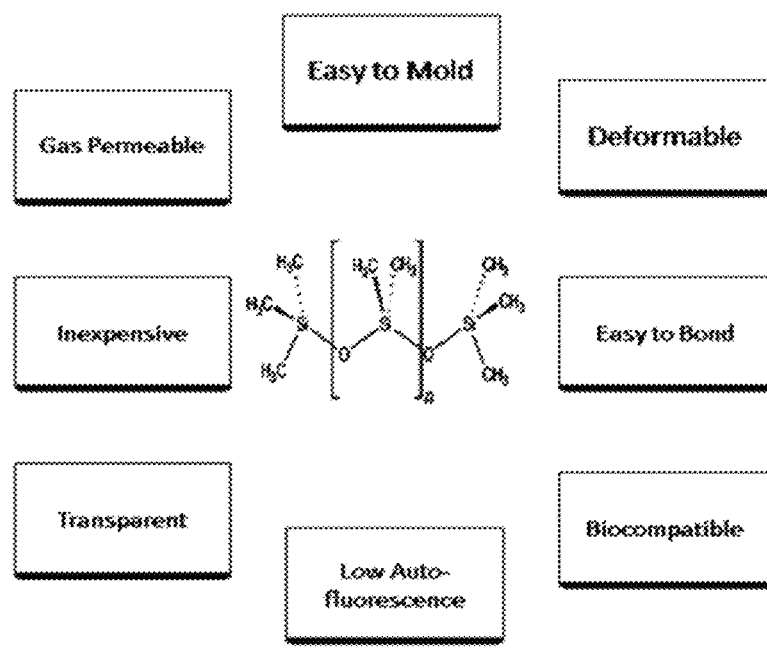

FIG. 18A-B presents the steps for fabricating a PDMS microphysiological system, (A); and the advantageous properties of PDMS, (B).

Figure 19:
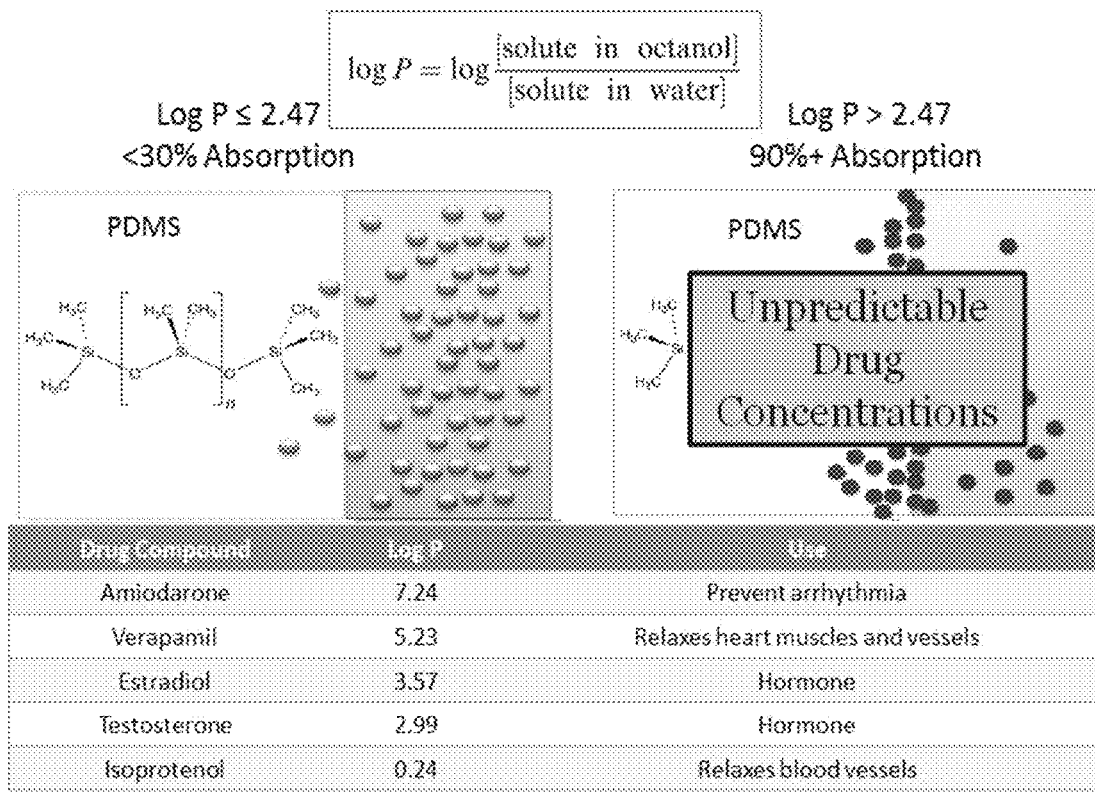

FIG. 19 demonstrates that drug absorption into PDMS and other polymers in MPSs may result in drug instability and unpredictable device performance. Accordingly, a universal coating is needed to keep drug concentrations consistent in order to reliably predict results in vivo.

Figure 20:
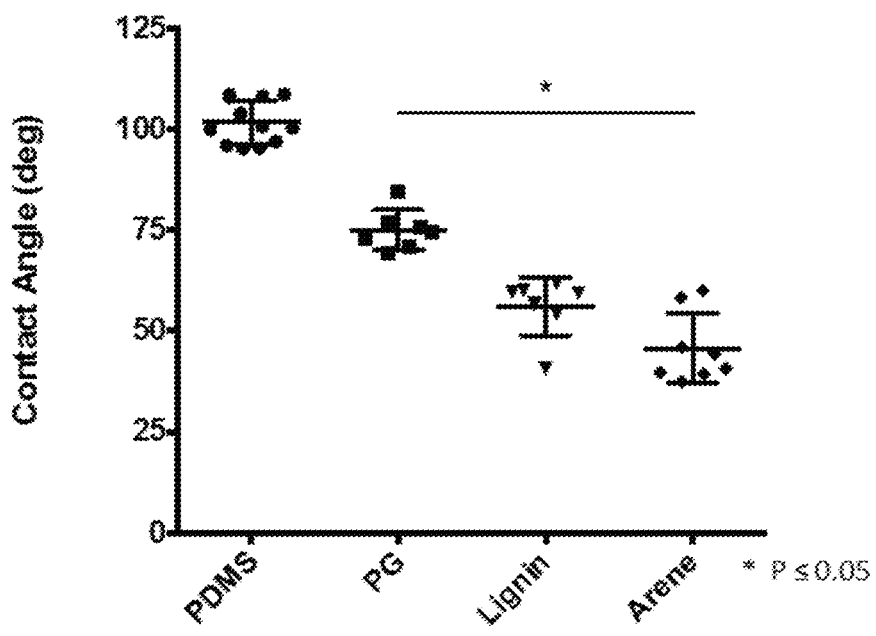

FIG. 20 shows that the macrocycle compositions of the disclosure (Arene), as well as pyrogallol and lignin increase the wettability of PDMS.

Figure 21:
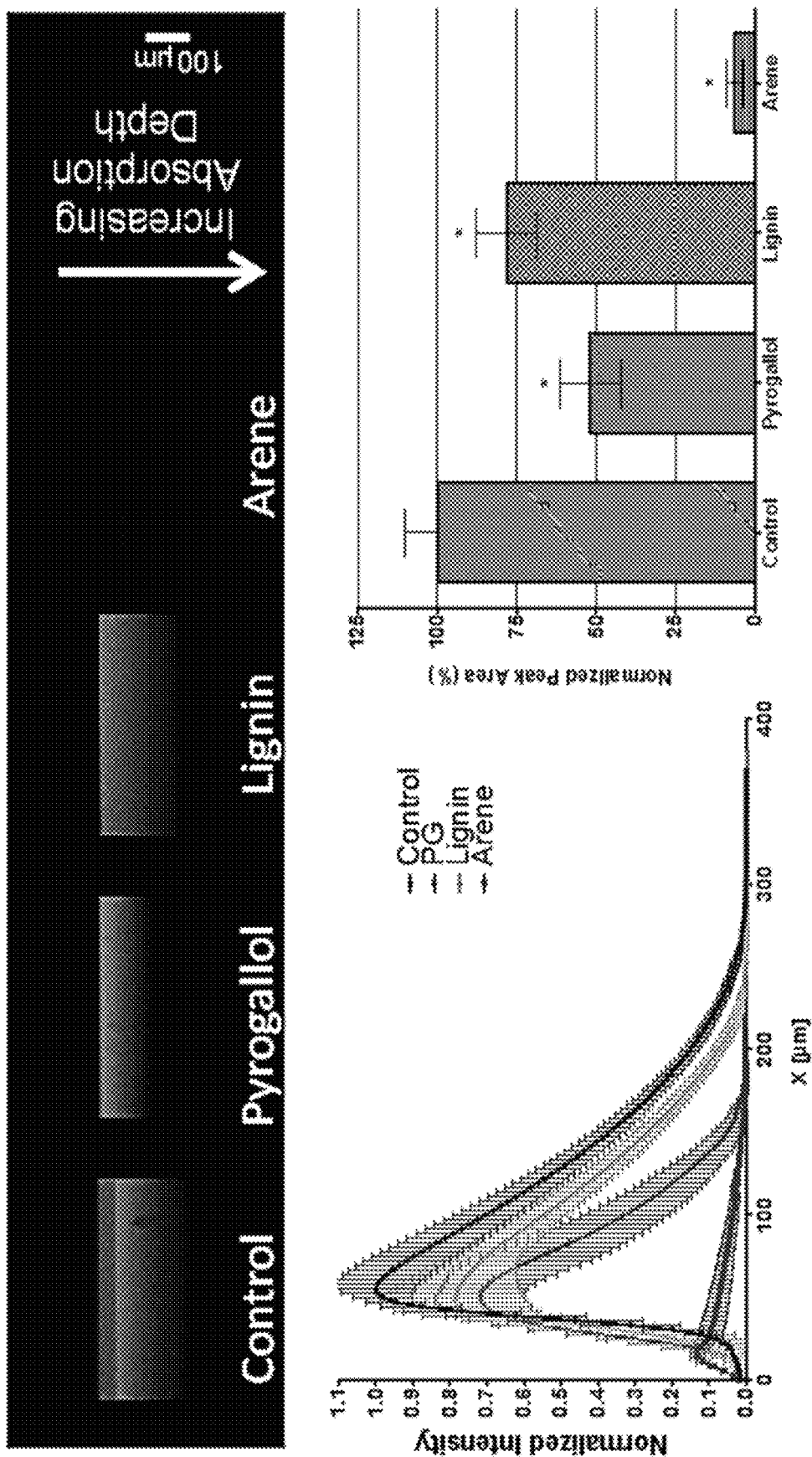

FIG. 21 demonstrates the effect of the macrocycle compositions of the disclosure (Arene) to prevent the absorption of hydrophobic molecules. Presented is an absorption peak area taken from submerged samples in Rhodamine B, a hydrophobic drug surrogate. Fluorescence of Rhodamine B was also imaged using a confocal microscope at a range of depths from the sample surface. More penetration of the molecule is marked by an increase in the area of the absorption profile and can be used to qualitatively compare coating performance. Absorbance has been normalized compared to the control (uncoated PDMS).

Figure 22:
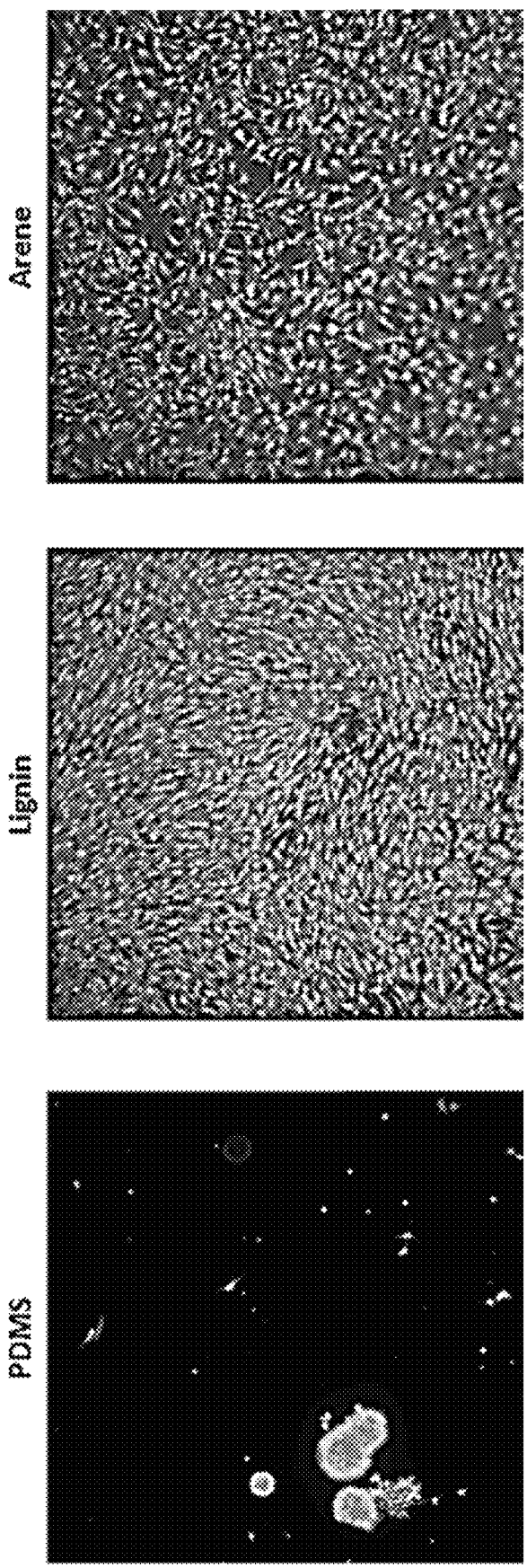

FIG. 22 presents confocal microscope images of the live staining of cells seeded on uncoated PDMS, lignin coated PDMS, and the macrocycle compositions of the disclosure (Arene) coated PDMS. PDMS does not show toxicity but low adherence. Lignin and Arene show increased adherence as well as no markers of toxicity.

Figure 23:
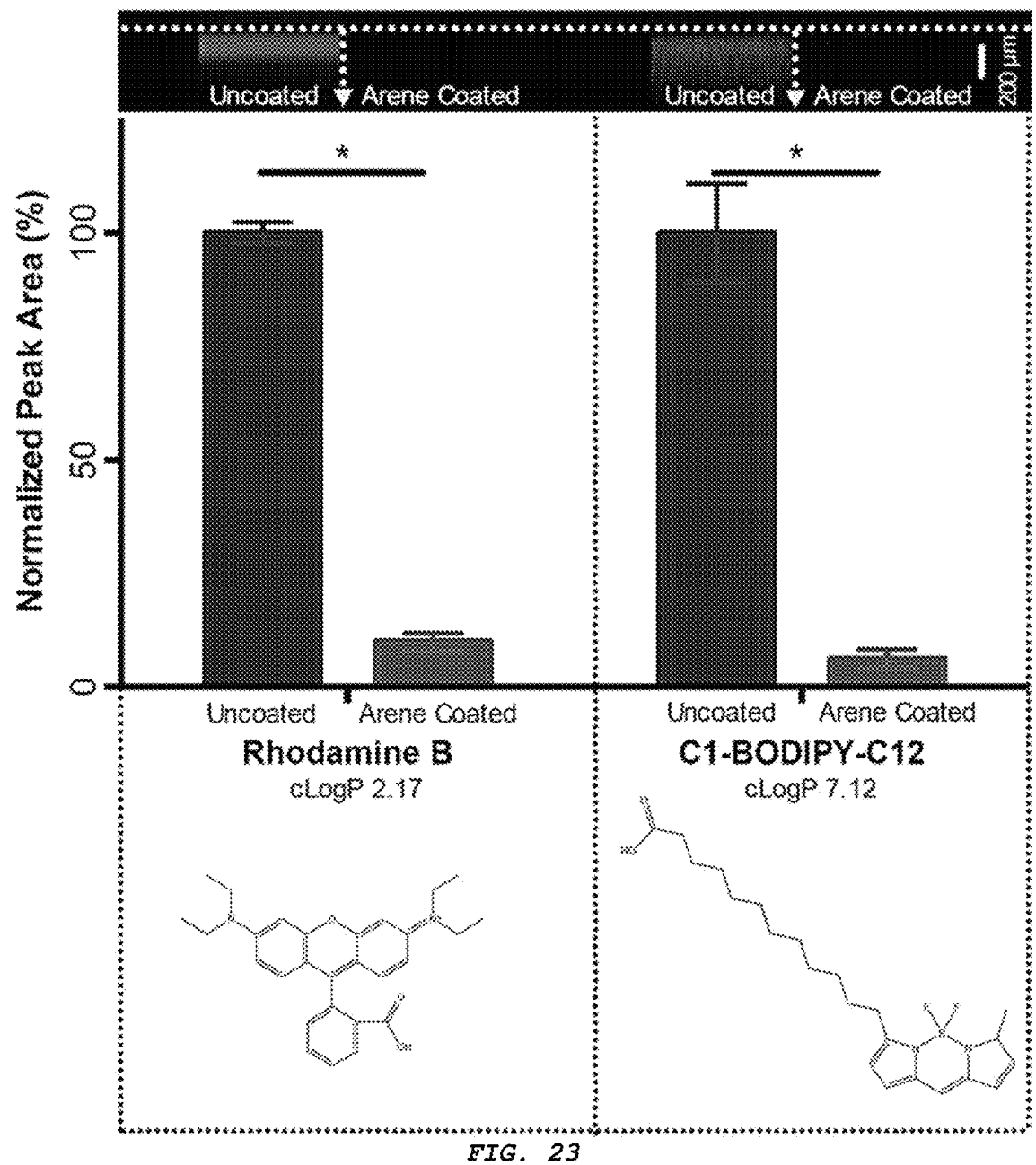

FIG. 23 shows the ability of Arene to block and be an effective barrio to diverse set of small molecules.

Figure 24:
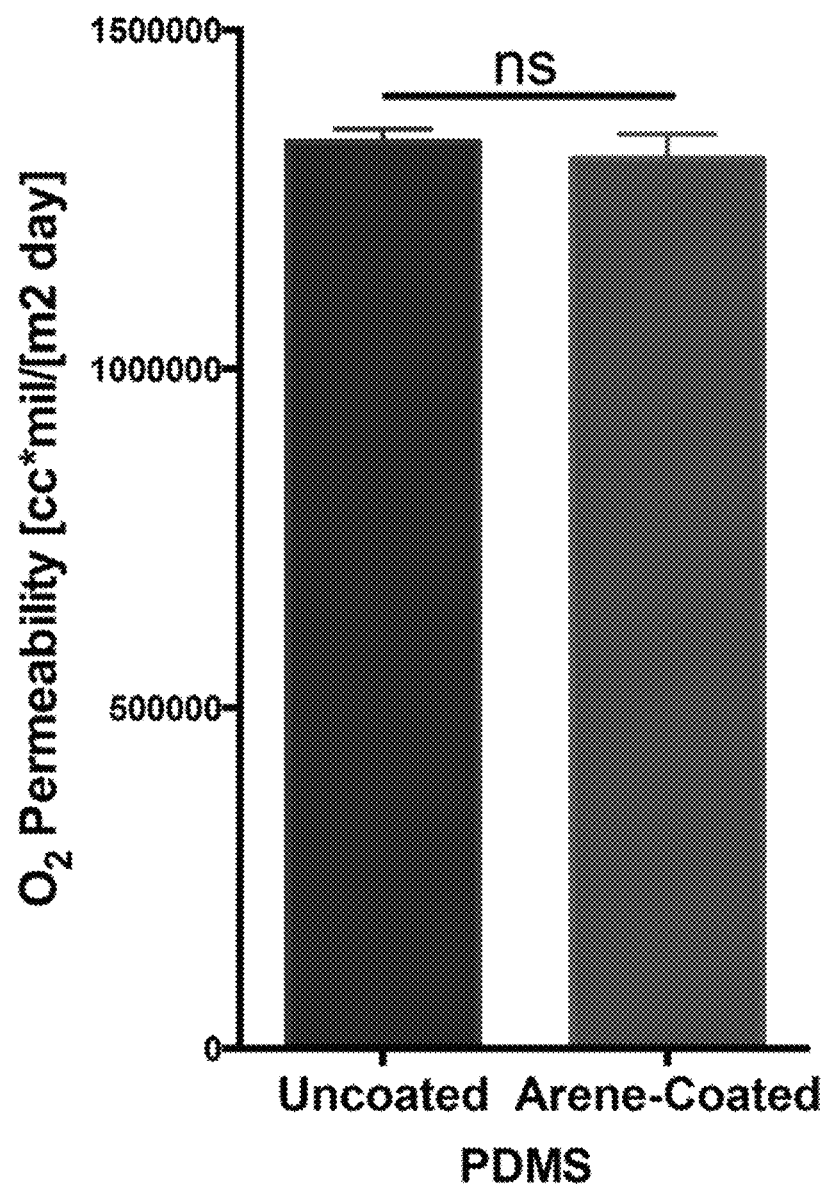

FIG. 24 shows that Arene coatings allow for oxygen transport.

DETAILED DESCRIPTION

As used herein and in the appended claims, the singular forms "a," "an," and "the" include plural referents unless the context clearly dictates otherwise. Thus, for example, reference to "a macrocycle" includes a plurality of such macrocycles and reference to "the salt" includes reference to one or more salts and equivalents thereof known to those skilled in the art, and so forth.

Unless defined otherwise, all technical and scientific terms used herein have the same meaning as commonly understood to one of ordinary skill in the art. Although there are many methods and reagents similar or equivalent to those described herein, the exemplary methods and materials are presented herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

Molecular screening of biological and chemical agents are performed in numerous laboratories and research institutes. Some of such screening methods utilize flow systems, microfluidics and culture systems that require exposure of the devices to the biological or chemical agents. Some of such devices absorb or adsorb or cause molecular changes in the agents being tested. One such material that is often used in the devices is PDMS. PDMS is easily manipulated and cost effective. However, PDMS is notorious for its ability to bind and absorb materials that contact it. Many laboratories have attempted to develop methods to solve the problem of absorption and swelling of PDMS in the presence of hydrophobic molecules and solvents. Glass microfluidic devices completely eliminate absorption while remaining biocompatible, but require expensive fabrication techniques and instrumentation, lack the gas permeability needed for microphysiologic cell culture, and cannot incorporate flexible structures or surfaces. One solution that has been proposed is to replace PDMS with casted poly(urethane) elastomers. Although, this elastomer shows many of the positive characteristics of PDMS, the castable polyurethanes explored cannot be easily released from silicon-SU-8 masters and therefore require additional steps in molding, including a PDMS molding step, significantly increasing costs. Additionally, the gas permeability needed for long term culture has not yet been investigated as the primary structure of polyurethanes significantly influences oxygen permeability. Other solutions focus on coating PDMS surfaces to prevent small molecule absorption. Silica sol-gel coatings were developed and showed great efficacy in preventing absorption of hydrophobic dyes, but the sol-gel coating effectively creates a glassy impermeable gas barrier making devices incompatible with cell culture. Additionally, the precursors, usually silanes such as methyltriethoxysilane (MTES), present severe health and safety hazards and are costly. Parylene coatings were also used to prevent the absorption of hydrophobic fluorescent dyes, but again these coatings create a virtually impermeable barrier to gases needed for cell culture and require expensive equipment and complicated deposition processes. Although these approaches and others present solutions for decreasing absorbance of molecules into PDMS, they do not allow for long term cell culture conditions needed in microphysiological systems that are able to support cells for up to a month. Other surface modification methods such as self-assembled monolayers and functionalized silanes have also been used, but again can only be employed on a small subset of substrates with great costs or complex processes. Therefore, the ideal solution would preserve the low cost of current PDMS devices, can be employed through a facile universal protocol, is biocompatible and gas permeable.

To further understand the present specification, certain terms are used and described as follows:

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

The term "alkyl", refers to an organic group that is comprised of carbon and hydrogen atoms that contain single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$ alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$ alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 12 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "cycloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 12 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cycloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 12 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "heterocycle", as used in this disclosure, refers to ring structures that contain at least 1 noncarbon ring atom. A "heterocycle" for the purposes of this disclosure encompass from 1 to 12 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings.

Examples of such bridged heterocycles include quinuclidine, diazabicyclo[2.2.1]heptane and 7-oxabicyclo[2.2.1] heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls. In a particular embodiment, the hydrocarbon is an aromatic hydrocarbon.

As used herein the term "inorganic polymer" refers to polymer or polymer network with a parent chain that does not include carbon atoms. Examples of inorganic polymers include, but are not limited to, polyphosphazenes, polysilicates, polysiloxanes, polysilanes, polysilazanes, polygermanes, and polysulfides.

As used herein the term "organic polymer" refers to polymer or polymer network with a parent chain that includes carbon atoms. Examples of inorganic polymers include, but are not limited to, polysiloxane and polyphsphazene.

As used herein "synthetic polymer" refers to polymers that are not found in nature. A wide variety of synthetic polymers are available that have variations in their parent chains and side chains. Examples of synthetic polymers, include polyacrylates, polyamides, polyesters, polyurethanes, polysulfides, and polycarbonates. A "synthetic polymer" may be an organic polymer or inorganic polymer, or vice versa.

The term "polymer" as used herein refers to a chemical compound that has a number of structural units linked together by covalent bonds. A structural unit is a group having two or more bonding sites. A bonding site may be created by the loss of an atom or group, such as H or OH, or by the breaking up of a double or triple bond, as when ethylene, $H_2C=CH_2$, is converted into a structural unit for polyethylene, $—H_2C—CH_2—$. In a linear polymer, the structural units are connected in a chain arrangement and thus need only be bifunctional, i.e., have two bonding sites. When the structural unit is trifunctional (has three bonding sites), a nonlinear, or branched, polymer results. Ethylene, styrene, and ethylene glycol are examples of bifunctional monomers, while glycerin and divinyl benzene are both polyfunctional. Polymers containing a single repeating unit, such as polyethylene, are called homopolymers. Polymers containing two or more different structural units, such as phenol-formaldehyde, are called copolymers. All polymers can be classified as either addition polymers or condensation polymers. An addition polymer is one in which the molecular formula of the repeating structural unit is identical to that of the monomer, e.g., polyethylene and polystyrene. A condensation polymer is one in which the repeating structural unit contains fewer atoms than that of the monomer or monomers because of the splitting off of water or some other substance, e.g., polyesters and polycarbonates. Many polymers occur in nature, such as silk, cellulose, natural rubber, and proteins. In addition, a large number of polymers have been synthesized in the laboratory, leading to such commercially important products as plastics, synthetic fibers, and synthetic rubber. Polymerization, the chemical process of forming polymers from their component monomers, is often a complex process that may be initiated or sustained by heat, pressure, or the presence of one or more catalysts.

The term "substituent" refers to an atom or group of atoms substituted in place of a hydrogen atom. For purposes of this disclosure, a substituent would include deuterium atoms.

The term "substantially" as used to modify a term means that the modified term includes minor variations in size, purity, structure and the like.

The term "substituted" with respect to hydrocarbons, heterocycles, and the like, refers to structures wherein the parent chain contains one or more substituents.

The term "unsubstituted" with respect to hydrocarbons, heterocycles, and the like, refers to structures wherein the parent chain contains no substituents.

The disclosure describes provides coating compositions, methods to prepare coating compositions and the uses thereof to coat a variety of surfaces, including polymeric surfaces. In a particular embodiment, the disclosure provides a simple dip-coating procedure with the coating compositions disclosed herein that allow for the formation of substrate independent (universal) coatings. The resultant coatings were found to be superior to other similar coatings in preventing absorbance of small molecules into a variety of organic and inorganic polymers including, for example, polymers such as poly(dimethyl siloxane) (PDMS). Therefore, the coating compositions of the disclosure are very beneficial for preventing drug absorbance into polymers used in drug screening devices, especially for the fast growing number of microphysiological systems based on PDMS. The virtues of PDMS include: ease in fabricating microphysiological systems (MPS), parallelization, optical transparency, and oxygen diffusion (e.g., see FIG. 18B). Accordingly, PDMS has seen widespread and predominant use in microdevice applications. Drug absorption into PDMS is a concern, however, as it leads to concentration and dosing predictability problems when using MPS for drug development and other applications. By preventing PDMS from adsorbing small molecules, such as drugs, would allow for PDMS devices to be used in organic synthesis reactions and analytical techniques that require a fixed concentration of analyte.

The disclosure demonstrates that the coating compositions of the disclosure were substrate independent and could universally be used to effectively coat a variety of organic and inorganic surfaces, including but not limited to, synthetic polymers, such as polycarbonate, nylon, polyether ether ketone, polystyrene, polyphenylene sulfide, poltetrafluoroethylene, and polydimethylsilane (e.g., see FIG. 11); metal surfaces, such as copper, and zinc (e.g., see FIGS. 12 and 13); and natural polymers and/or mineral surfaces, including cellulose (wood), keratin (nails), conchins (mussels), and calcium carbonate (Coral) (e.g., see FIGS. 14 and 15).

Furthermore, it was found that coatings comprising the compositions described herein were able to prevent or restrict the absorbance of small molecules on and/or into polymeric surfaces. Moreover, the coating compositions were equally effective whether the polymers were synthetic polymers (e.g., poly(dimethylsiloxane (PDMS)), or natural polymers (e.g., rubber).

In a certain embodiment the disclosure provides for a coating composition or methods for preparing a coating composition which comprises one or more macrocycles having the structure of Formula I:

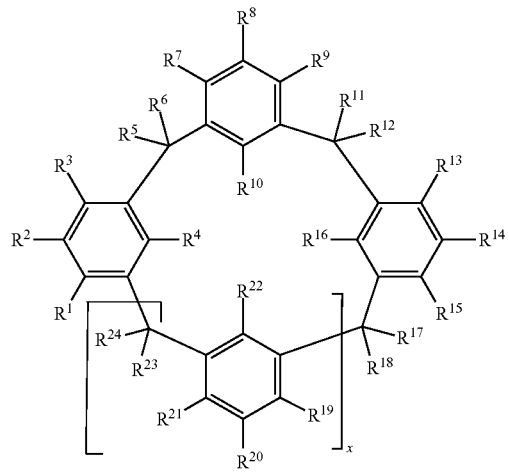

Formula I wherein, $R^1$-$R^{24}$ are independently selected from the group consisting of H, optionally substituted alkyl, optionally substituted hetero-alkyl, optionally substituted alkenyl, optionally substituted hetero-alkenyl, optionally substituted alkynyl, optionally substituted hetero-alkynyl, optionally substituted cycloalkyl, optionally substituted cycloalkenyl, optionally substituted aryl, optionally substituted heterocycle, hydroxyl, halo, alkoxy, aldehyde, carbonyl, carboxyl, ester, amino, amido, azido, cyano, thiol, sulfonyl, sulfo, and sulfinyl; and wherein x is an integer selected from 1, 2, 3, 4, 5, 6, 7, 8, 9, 10, 11, 12, 13, 14, and 15, or a range including any two of the foregoing integers.

In a further embodiment the disclosure provides for a coating composition or methods of preparing a coating composition which comprises one or more macrocycles having the structure of Formula I:

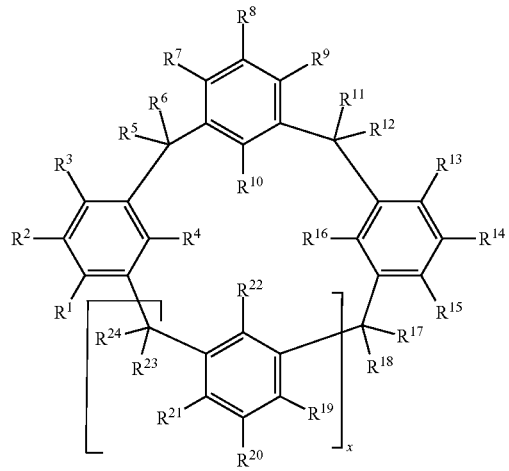

Formula I wherein, $R^1$-$R^{24}$ are independently selected from the group consisting of H, optionally substituted ($C_1$-$C_6$)alkyl, hydroxyl, halo, (C$_1$-C$_5$)alkoxy, aldehyde, carbonyl, carboxyl, ester; and x is an integer selected from 1, 2, 3, and 4, or a range including any two of the foregoing integers.

In another embodiment, the disclosure provides for a coating composition or methods of preparing a coating composition which comprises one or more macrocycles having the structure of Formula I(a):

Formula I (a)

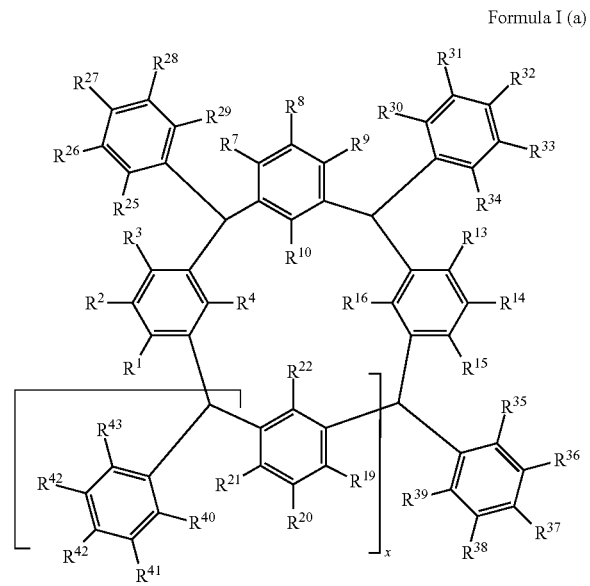

wherein, R$^1$-R$^4$, R$^7$-R$^{10}$, R$^{13}$-R$^{16}$, R$^{19}$-R$^{22}$, and R$^{25}$-R$^{43}$ are independently selected from the group consisting of H, optionally substituted (C$_1$-C$_6$)alkyl, hydroxyl, halo, (C$_1$-C$_5$) alkoxy, aldehyde, carbonyl, carboxyl, ester; and x is an integer selected from 1, 2, 3, 4, 5, 6, 7, 8, 9, 10, 11, 12, 13, 14, and 15, or a range including any two of the foregoing integers.

In yet a further embodiment, the disclosure provides for a coating composition or methods of preparing a coating composition which comprises one or more macrocycles having the structure of:

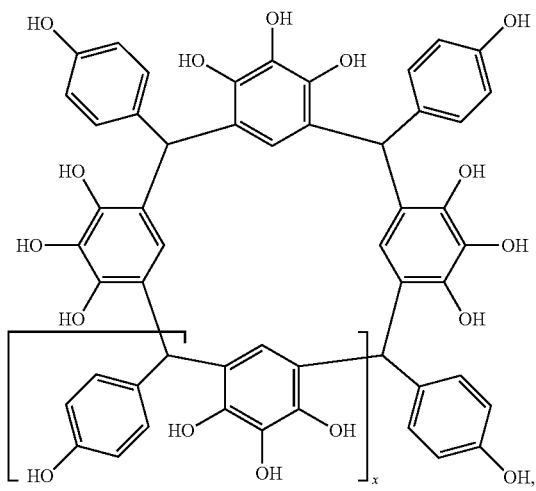

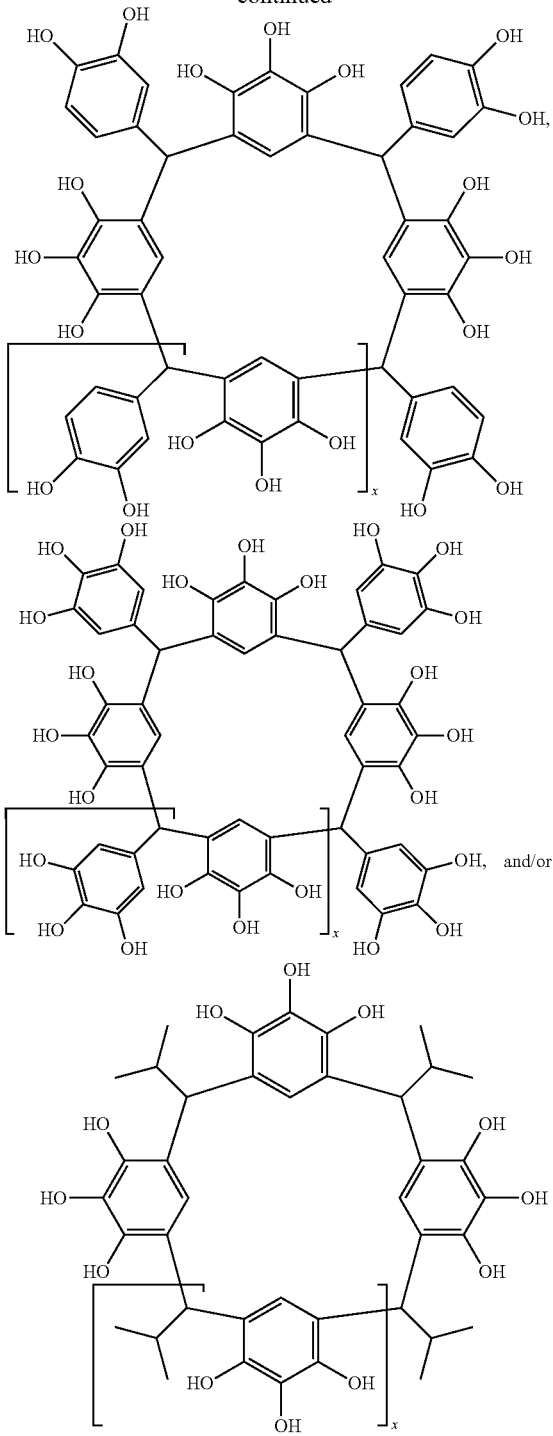

wherein, x is an integer selected from 1, 2, 3, 4, or a range including any two of the foregoing integers.

In certain embodiment, a coating composition or method of making a coating composition comprises one or more macrocycles disclosed herein which has been dissolved in an organic solvent. In a further embodiment, one or more macrocycles of the disclosure are dissolved in a polar aprotic solvent. Examples of polar aprotic solvents include but are not limited to, dichloromethane, tetrahydrofuran, ethyl acetate, dimethyl sulfoxide, acetone, acetonitrile, and N,N-dimethylformamide. In a particular embodiment, the coating composition comprises 0.5 mg/mL, 0.75 mg/mL, 1.0 mg/mL, 1.5 mg/mL, 2 mg/mL, 2.5 mg/mL, 3 mg/mL, 3.5 mg/mL, 4 mg/mL, 4.5 mg/mL, or a range between any two of the foregoing values, of one more macrocycles disclosed herein.

In a particular embodiment, the disclosure provides for a coating composition or methods of preparing a coating composition which comprises a buffered aqueous solution comprising one or more salts. In a further embodiment, the one or more salts comprise alkali metals, alkaline earth metals, and/or transition metals. In yet a further embodiment, the one or more salts comprises halide atoms, such as chlorides. Examples of such salts include but are not limited to, NaCl, $CaCl_2$, $MgCl_2$, $CuCl_2$, $FeCl_2$, or a mixture of any of the foregoing. In a certain embodiment, the coating compositions of the disclosure comprise 0.05M, 0.1M, 0.15M, 0.2M, 0.25M, 0.3M, 0.35M, 0.4M, 0.45M, 0.5M, 0.55M, 0.6M, 0.65M, 0.7M, 0.75M, 0.8M, 0.85M, 0.9M, 1M, 1.1M, 1.2M, 1.3M, 1.4M, 1.5M, 1.6M, 1.7M, 1.75M, 1.8M, 1.9M, 2.0M, 2.1M, 2.2M, 2.3M, 2.4M, 2.5M, 2.6M, 2.7M, 2.8M, 2.9M, 3.0M, 3.5M, 4M, 4.5M, 5.0M, or a range between any two of the foregoing molarity numbers, of salts.

In a further embodiment, the disclosure provides for a coating composition which comprises a buffered aqueous solution. Examples of buffered aqueous solutions include but are not limited to, phosphate buffered saline, tris-buffered saline, bicine, tricine, glycinamide, 3-[[1,3-dihydroxy-2-(hydroxymethyl)propan-2-yl]amino]propane-1-sulfonic acid (TAPS), 3-[4-(2-hydroxyethyl)piperazin-1-yl]propane-1-sulfonic acid (HEPPS), N-(2-Hydroxyethyl)-piperazine-N'-2-hydroxypropanesulfonic acid (HEPPSO), iperazine-1,4-bis(2-hydroxypropanesulfonic acid) dihydrate, piperazine-N,N'-bis(2-hydroxypropanesulfonic acid) (POPSO), 3-[[1,3-dihydroxy-2-(hydroxymethyl)propan-2-yl]amino]-2-hydroxypropane-1-sulfonic acid (TAPSO), 3-(N,N-Bis[2-hydroxyethyl]amino)-2-hydroxypropane-sulfonic acid (DIPSO), (4-(2-hydroxyethyl)-1-piperazineethanesulfonic acid) (HEPES), 2-[[1,3-dihydroxy-2-(hydroxymethyl)propan-2-yl]amino]ethanesulfonic acid (TES), N,N-Bis(2-hydroxyethyl)-2-aminoethanesulfonic acid, N,N-Bis(2-hydroxyethyl)taurine (BES), (3-(N-morpholino)propanesulfonic acid) (MOPS), 3-morpholino-2-hydroxypropanesulfonic acid (MOPSO), piperazine-N,N'-bis(2-ethanesulfonic acid) (PIPES), or a mixture of any of the foregoing. In a further embodiment, the pH of the buffered aqueous solution is dependent on the precursor molecule and salt chosen but is typically somewhat basic. In another embodiment, the buffered aqueous solution has a pH of 6, 6.5, 7, 7.5, 8, 8.5, 9, 9.5, 10, 10.5, or 11, or a range between any two of the foregoing pH numbers.

In a particular embodiment, the disclosure provides for a coating composition which comprises one or more macrocycles dissolved in a polar aprotic solvent that has been added to a buffered aqueous solution comprising a salt. In a further embodiment, the disclosure provides for a coating composition which comprises one or more macrocycles disclosed herein (e.g., Formula I or I(a)) and $MgCl_2$ in Bicine buffer, wherein the buffer has a pH from 6 to 9.

The disclosure demonstrates that the coatings provided by the compositions of the disclosure were biocompatible, gas permeable, and prevented the absorption of small molecules by the polymeric material. Accordingly, the coating compositions of disclosure are ideally suited for coating polymeric surfaces used in drug screening (e.g., microfluidic devices, hollow fiber bioreactors, microphysiological systems); tissue culture (e.g., tissue culture flasks and plates); laboratory equipment and supplies (e.g., conical tubes, pipette tips, Eppendorf tubes, etc.); implantable devices (e.g., implanted pumps, stents, dentures, catheters etc.); or any other device, equipment, or item which would benefit from the same.

In a particular embodiment, the disclosure provides for use of the coating compositions described herein to coat one or more surfaces of a microfluidic device. A small but not limiting sampling of microfluidic devices includes inkjet printheads, DNA chips, lab-on-a-chip technology, micro-propulsion systems and micro-thermal systems. Microfluidics devices provide precise control of manipulation of fluids that are geometrically constrained to a small, typically sub-millimeter, scale. Typically, fluids are moved, mixed, separated or otherwise processed by the microfluidic device.

Processes which are normally carried out in a laboratory can be miniaturized on a lab-on-a-chip microfluidic device in order to enhance efficiency and mobility as well as reduce sample and reagent volumes. Particular examples of these lab-on-a chip microfluidic devices include organ-on-a-chip or micro-physiological systems (MPSs). MPSs can be used to combine genetically relevant cell lines in micro-environments that recapitulate not only organ specific structure, but also organ system relationships.

Most MPSs are easily manufactured using well known lithography techniques (e.g., see FIG. 18A). Briefly, photoresist is spin coated onto a silicon wafer, a mask is used to expose specific features to UV radiation to crosslink the photoresist. The un-crosslinked photoresist is then removed with a solvent. Polydimethylsiloxane (PDMS) is poured over the wafer to create a negative of the features. The features can be custom designed, for example, to hold cells or biological agents in chambers wherein the chambers can include inlets and outlets for media perfusion or buffer flow. PDMS has many characteristics that make it the most popular candidate for producing MPS devices. PDMS is easily crosslinked by mixing a base with the cross-linker and heating in an oven for a few hours. After crosslinking, the PDMS has shown to be biologically compatible and amenable to many standard cell culture techniques due to its transparency, oxygen permeability, and low auto-fluorescence. Devices can be produced inexpensively with highly precise reproducible structures. Additional methods to fabricate microfluidic devices can be used with the coating compositions of the disclosure, including those described in U.S. patent application Ser. No. 08/131,841, filed Oct. 4, 1993, entitled "Formation of Microstamped Patterns on Surfaces and Derivative Articles," by Kumar, et al., now U.S. Pat. No. 5,512,131, issued Apr. 30, 1996; U.S. patent application Ser. No. 09/004,583, filed Jan. 8, 1998, entitled "Method of Forming Articles including Waveguides via Capillary Micromolding and Microtransfer Molding," by Kim, et al., now U.S. Pat. No. 6,355,198, issued Mar. 12, 2002; International Patent Application No. PCT/US96/03073, filed Mar. 1, 1996, entitled "Microcontact Printing on Surfaces and Derivative Articles," by Whitesides, et al., published as WO 96/29629 on Jun. 26, 1996; International Patent Application No.: PCT/US01/16973, filed May 25, 2001, entitled "Microfluidic Systems including Three-Dimensionally Arrayed Channel Networks," by Anderson, et al., published as WO 01/89787 on Nov. 29, 2001; U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," by Stone, et al., published as U.S. Patent Application Publication No. 2005/0172476 on Aug. 11, 2005; International Patent Application No. PCT/US2006/007772, filed Mar. 3, 2006, entitled "Method and Apparatus for Forming Multiple Emulsions," by Weitz, et al., published as WO 2006/096571 on Sep. 14, 2006; U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007; and U.S. patent application Ser. No. 11/368,263, filed Mar. 3, 2006, entitled "Systems and Methods of Forming Particles," by Garstecki, et al. Also incorporated herein by reference are U.S. Provisional Patent Application Ser. No. 60/920,574, filed Mar. 28, 2007, entitled "Multiple Emulsions and Techniques for Formation," by Chu, et al.; U.S. patent application Ser. No. 12/058,628, filed on Mar. 28, 2008, entitled "Emulsions and Techniques for Formation," by Chu, et al.; PCT Patent Application No. PCT/US2008/004097, filed on Mar. 28, 2008, entitled "Emulsions and Techniques for Formation," by Chu, et al.; and U.S. Provisional Patent Application Ser. No. 60/963,709, filed Aug. 7, 2007, entitled "Metal Oxide Coating on Surfaces," by Weitz, et al. (all of the foregoing are incorporated herein by reference).

Although PDMS has several positive attributes (e.g., see FIG. 18B), PDMS adsorbs hydrophobic molecules due to its hydrophobicity. Specifically, it has been found that molecules with a Log P value above 2.47 will partition into the PDMS to produce unpredictable concentrations in cell and media channels making it impossible to predict the actual dosing concentrations for drug investigations. This unpredictability is an obstacle for using such devices for biological studies including, but not limited to, organ-on-a-chip devices to screen for drug candidates in discovery stages.

Accordingly, the coating compositions of the disclosure are beneficial for preventing drug absorbance into polymers used in drug screening devices. Especially for the fast growing number of microphysiological systems based on PDMS. The virtues of PDMS including ease of making the microphysiological systems (MPS), parallelization, optical transparency, and oxygen diffusion in combination with the coatings described herein can open up new avenues for research with these devices as well as provide more predictive results for drug development.

Surfaces of substrates, such as the interior surfaces of microfluidic devices, may be modified with the coating compositions disclosed herein so as to significantly increase the chemical compatibility of the devices. The coating may be applied to the surfaces (e.g., inner surface) by, for example, dip coating or spin coating. In particular, the coating compositions of the disclosure can be applied to any polymeric or nonpolymeric surface. Polymeric surfaces can be prepared in any number of suitable methods. For example, a flat, curved, grooved, pitched, and any other type of surface can be formed. In some embodiments, one or more channels can be formed on a pre-existing polymeric surface or within the bulk of the polymer, for example, by contacting a polymer surface having one or more channels with a flat polymer surface. Other suitable techniques for forming polymer surfaces will be readily apparent to one of ordinary skill in the art. The size of the polymer surface formed thereon and/or therein is not limited. The size of the polymer surface that can be used with the coating compositions of the disclosure can be several nanometers to many meters in dimension.

In a particular embodiment, the disclosure provides for coating one or more surfaces or parts of a surface comprising coating the surface with a coating composition disclosed herein. In a further embodiment, the disclosure provides for coating one or more surfaces or parts of a surface by dipping the surface to be coated in a coating composition disclosed. In an alternate embodiment, the disclosure provides for coating one or more surfaces or parts of a surface by spraying, depositing, painting, spreading, or spinning the coating composition on the surface. In yet a further embodiment, at least one of the surfaces or parts of the surface is comprised of a polymeric material. In another embodiment, at least one of the surfaces or parts of the surface is comprised of a synthetic polymeric material. In yet another embodiment, at least one of the surfaces or parts of the surface is comprised of a PDMS. In a further embodiment, at least one of the surfaces or parts of the surface is part of a microfluidic device.

The following examples are intended to illustrate but not limit the disclosure. While they are typical of those that might be used, other procedures known to those skilled in the art may alternatively be used.

EXAMPLES

Example 1

Figure 1:
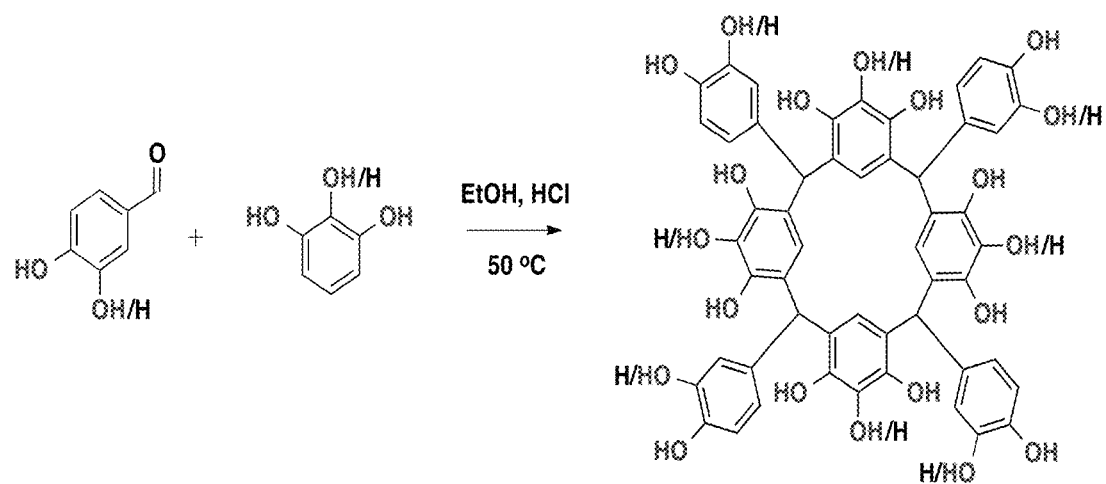
FIG. 1 presents an exemplary scheme that can be used to synthesize polyphenolic macrocycles which can be incorporated into the coating compositions disclosed herein.
Figure 2:
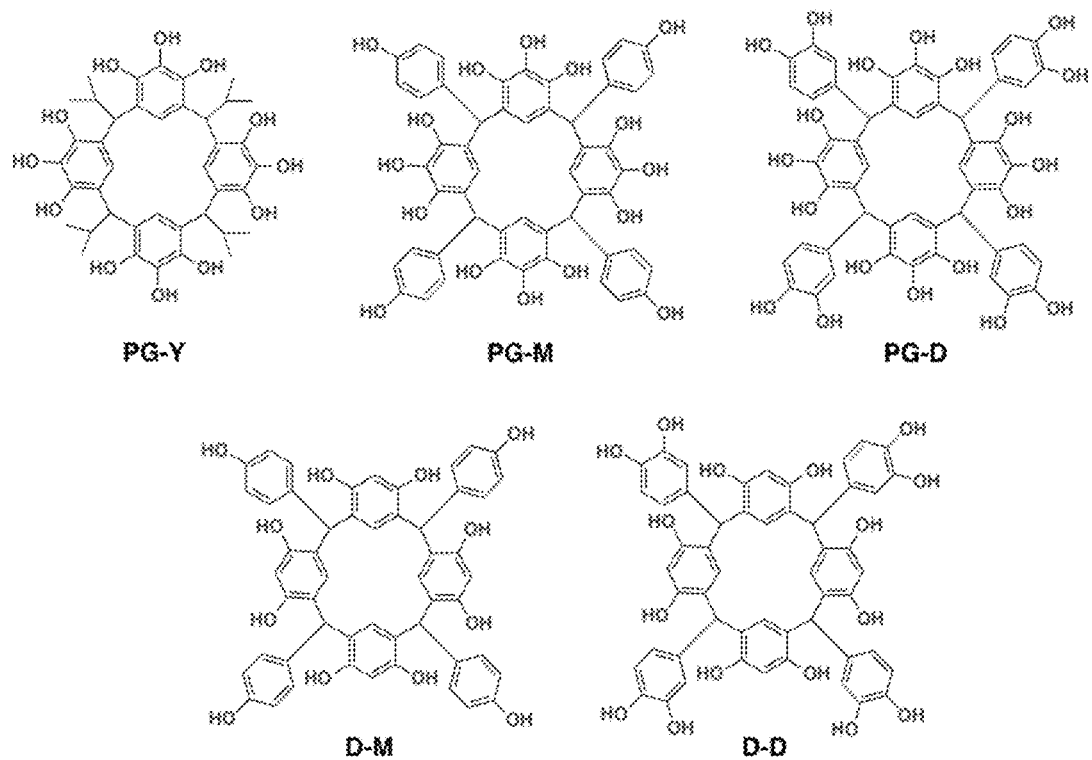
FIG. 2 presents exemplary polyphenolic macrocycles that can be used with coating compositions of the disclosure.
Figure 3:
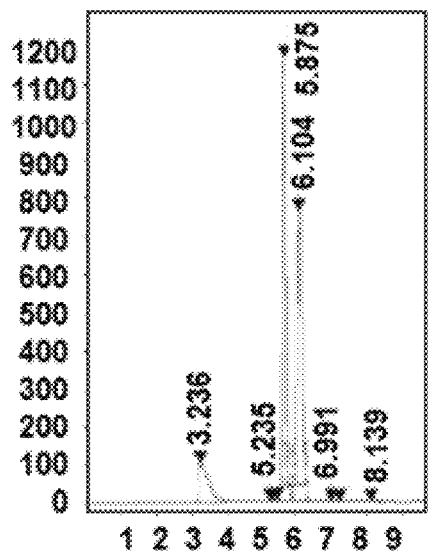
FIG. 3 provides HS-MS, NMR and HPLC analyses of the macrocycles disclosed in FIG. 2.
Figure 4:
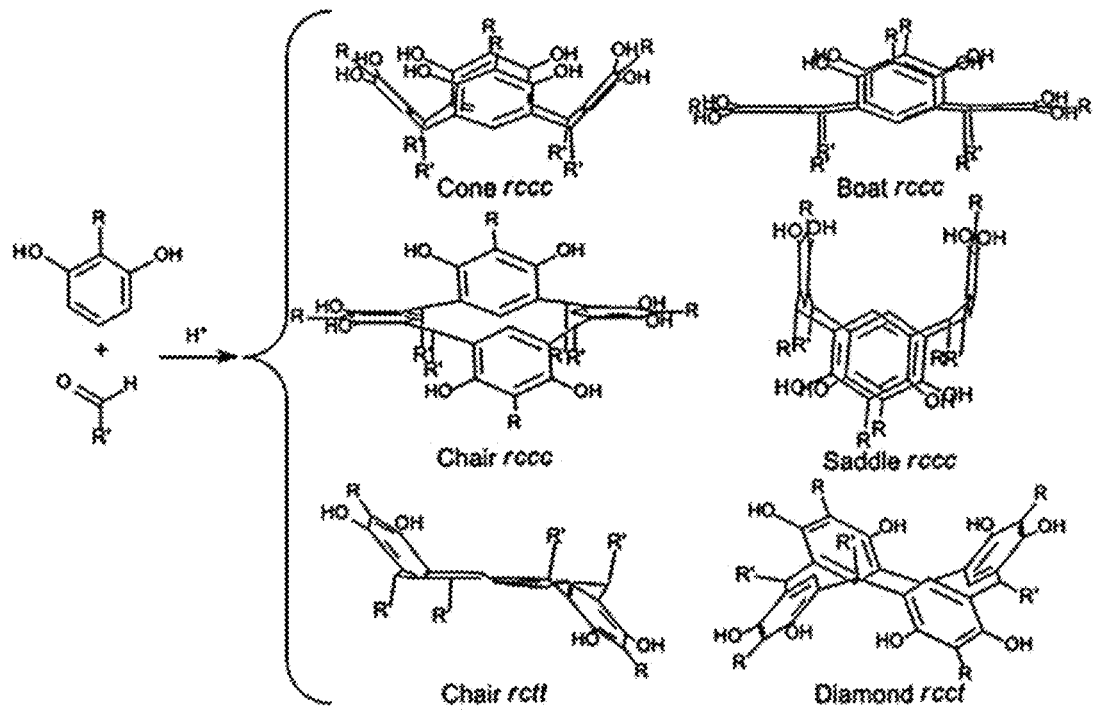
FIG. 4 illustrates the possible conformations for the exemplary polyphenolic macrocycles.
Figure 5:
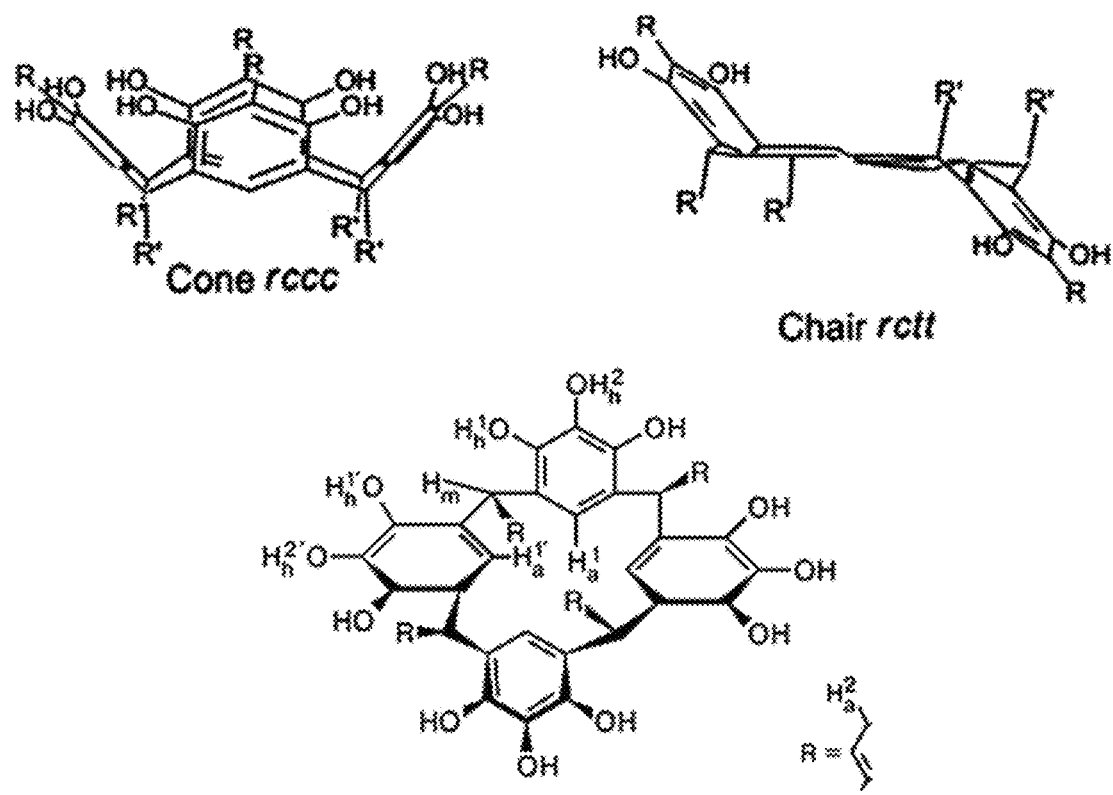
FIG. 5 provides a close up view of the Cone rccc and Chair rctt conformations of polyphenolic macrocycles.
Figure 6:
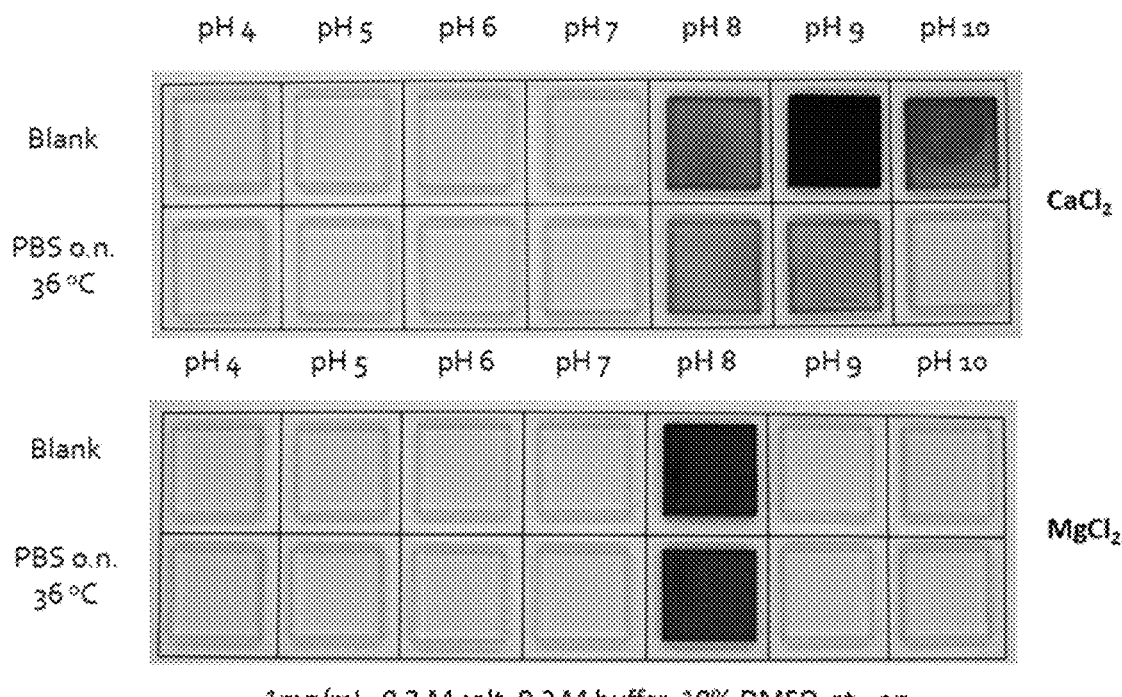
FIG. 6 displays a pH screen using a coating composition comprising the D-D macrocycle and two different salts at various pHs. The stability of the coating was tested by incubating the coatings overnight in PBS at 36° C. The darker the color the more coating that has remained. The screen indicates that between pH 8 to 9 is optimal for coating compositions comprising the D-D macrocycle and $CaCl_2$ salt, while pH 8.0 is optimal for the D-D macrocycle and $MgCl_2$ salt.
Figure 7:
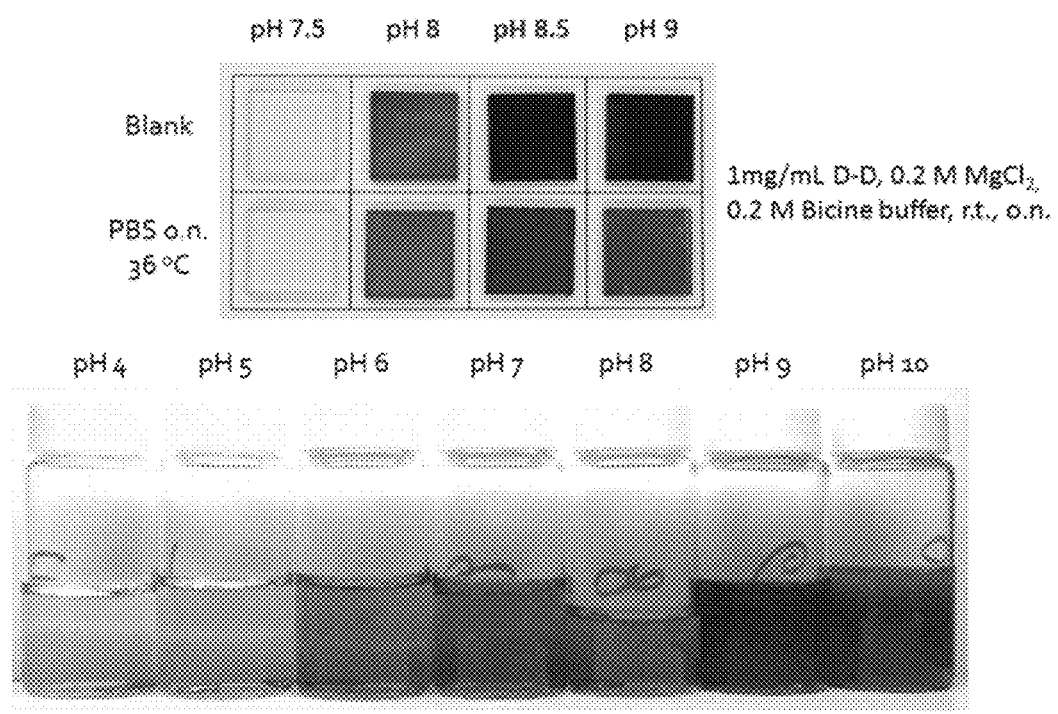
FIG. 7 displays the results of a pH optimization assay comprising the D-D macrocycle and 0.2 M $MgCl_2$ at various pHs. It was determined that a pH 8.5 is optimal for the D-D macrocycle and 0.2M $MgCl_2$ in Bicine buffer. The stability of the coating was tested by incubating the coatings overnight in PBS at 36° C. The darker the color the more coating that has remained.
Figure 8:
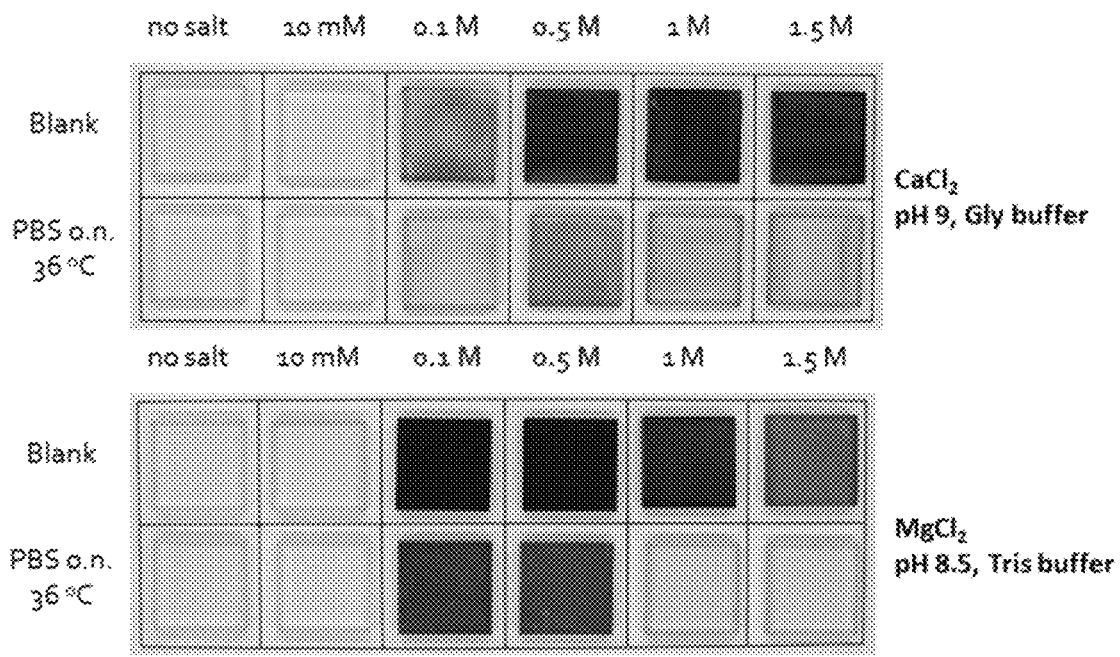
FIG. 8 displays a screen with different salt concentrations with a coating composition comprising the D-D macrocycle and two different salts at pH 9 or pH 8.5. The stability of the coating was tested by incubating the coatings overnight in PBS at 36° C. The darker the color the more coating that has remained. The screen indicates that a salt concentration of 0.5 M is optimal for $CaCL_2$ in Gly buffer, while a salt concentration between 0.1M to 0.5M is optimal for $MgCl_2$ in Tris buffer.
Figure 9:
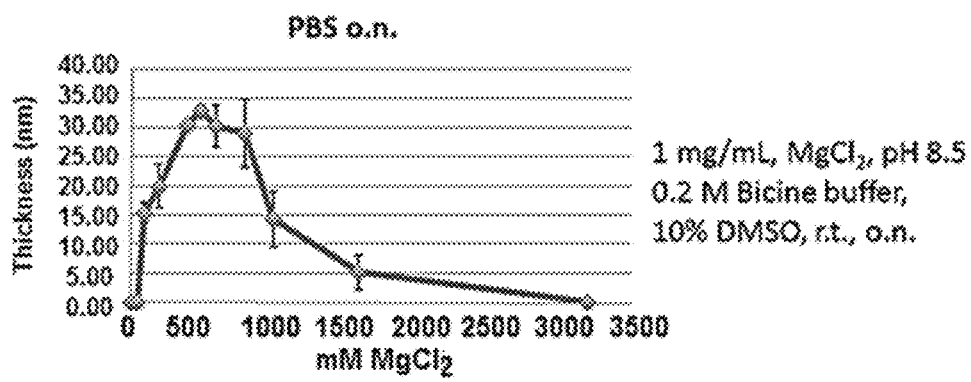
FIG. 9 displays the results of an optimization assay comprising the D-D macrocycle at pH 8.5 using various $MgCl_2$ salt concentrations. A salt concentration of 0.5M was found to be optimal for the D-D macrocycle in Bicine buffer. The stability of the coating was tested by incubating the coatings overnight in PBS at 36° C. The darker the color the more coating that has remained.
Figure 9:
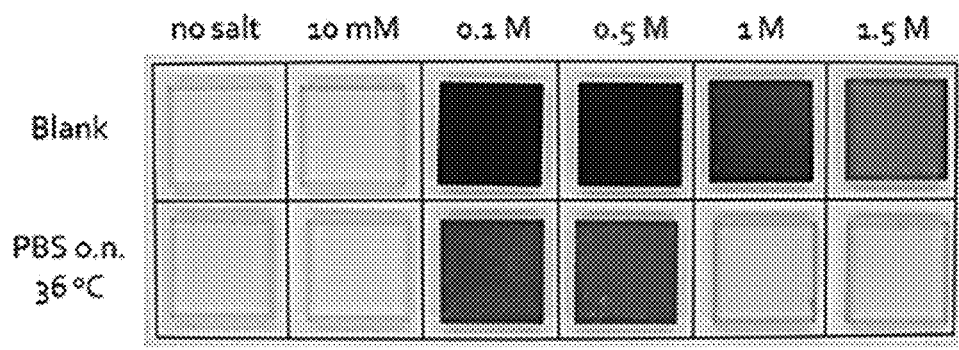

Synthesis of Macrocycles. The macrocycles of disclosure were synthesized using methods described in *Acta Cryst.* 2007, 03533 and *Chem. Commun.* 2009, 7497. Briefly, a 3,4-dihydroxybenzaldehyde or 4-hydroxybenzaldehyde was reacted with a 1,2,3-trihydroxybenzene or 1,2-dihdyroxybenzene in ethanol and a catalytic amount of hydrochloric acid at 50° C. for at least 30 minutes (e.g., see FIG. 1). Additional macrocycles can be made using the same reaction conditions but varying the reactant structure (e.g., see FIG. 2).

Calix[4]arene 1:

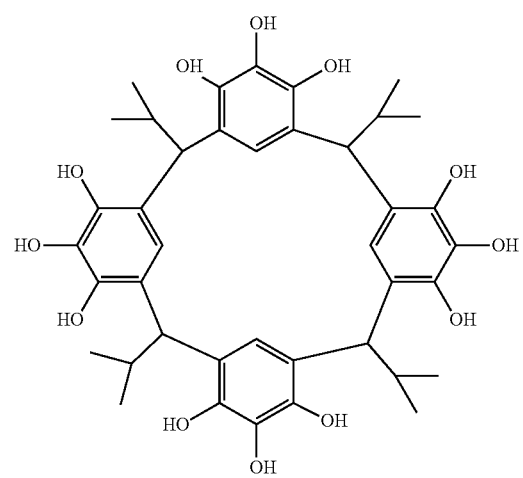 [SMILES: CC(C)C1c2cc(c(O)c(O)c2O)C(C(C)C)c2cc(c(O)c(O)c2O)C(C(C)C)c2cc(c(O)c(O)c2O)C(C(C)C)c2cc1c(O)c(O)c2O]

Calix[4]arene 1 was synthesized following an established procedure and the analytical data was in accordance with the literature.

Calix[4]arene 2:

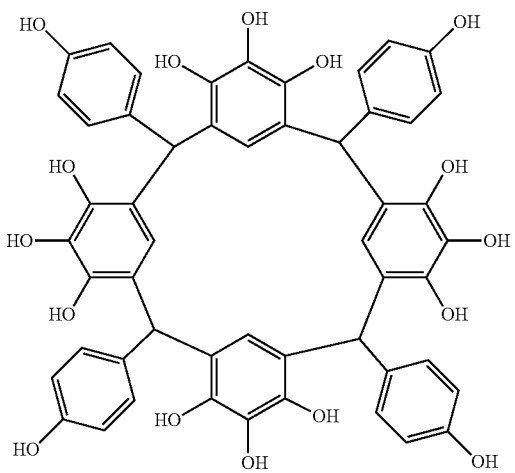 [SMILES: Oc1ccc(C2c3cc(c(O)c(O)c3O)C(c3ccc(O)cc3)c3cc(c(O)c(O)c3O)C(c3ccc(O)cc3)c3cc(c(O)c(O)c3O)C(c3ccc(O)cc3)c3cc2c(O)c(O)c3O)cc1]

Calix[4]arene 2 was synthesized following an established procedure and the analytical data was in accordance with the literature.

Calix[4]arene 3:

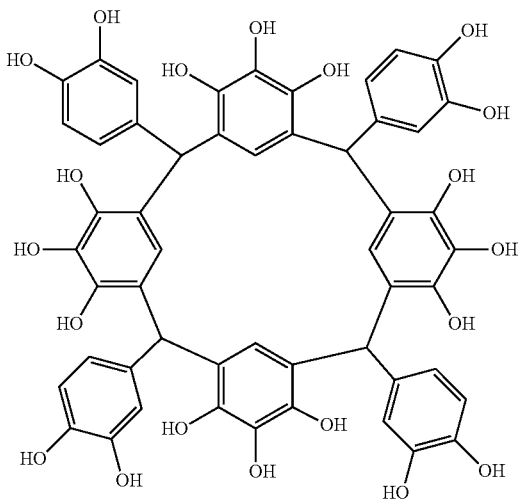 [SMILES: Oc1ccc(C2c3cc(c(O)c(O)c3O)C(c3ccc(O)c(O)c3)c3cc(c(O)c(O)c3O)C(c3ccc(O)c(O)c3)c3cc(c(O)c(O)c3O)C(c3ccc(O)c(O)c3)c3cc2c(O)c(O)c3O)cc1O]

Pyrogallol (11.0 g, 87.3 mmol, 1.00 equiv.) and 3,4-dihydroxybenzaldehyde (12.1 g, 87.3 mmol, 1.00 equiv.) were dissolved in a mixture of EtOH, $H_2O$ and concentrated HCl solution (3:1:1, 275 mL). The mixture was then stirred at 50° C. for 2 d. Cold $H_2O$ (100 mL) where added and the mixture was allowed to cool to 4° C. before it was centrifuged and the supernatant was removed. The residue was dissolved and DMF (10 mL), then $H_2O$ (100 mL) was added and the mixture was allowed to cool to 4° C., prior to centrifugation. This process was repeated 4 more times. The residue was then lyophilized to yield the calix[4]arene 3 isomeric mixture as red powder (38%, 8.21 g).

HRMS ESI-TOF calcd. for $C_{52}H_{40}NaO_{20}$ (100%, [M+Na]$^+$): 1007.2001; found 1007.1981.

Calix[4]arene 4:

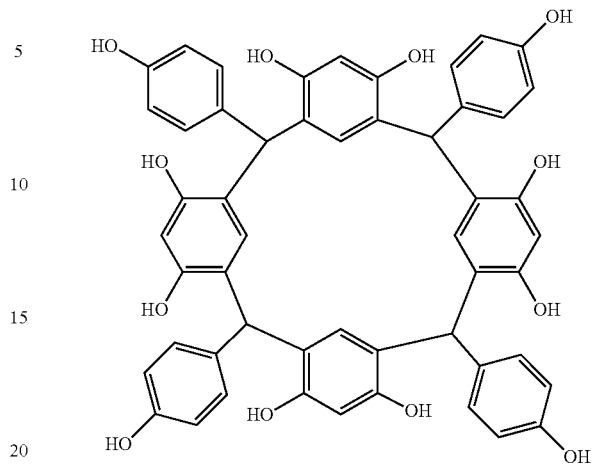

Resorcinol (7.97 g, 72.5 mmol, 1.00 equiv.) and para-hydroxybenzaldehyde (8.72 g, 72.5 mmol, 1.00 equiv.) were dissolved in a mixture of EtOH, $H_2O$ and concentrated HCl solution (3:1:1, 275 mL). The mixture was then stirred at 50° C. for 15 h. The mixture was allowed to cool to 4° C. before it was centrifuged and the supernatant was removed. The residue was suspended in water and centrifuged again. This process was repeated 5 more times. The residue was then lyophilized to yield the calix[4]arene 4 isomeric mixture as red powder (71%, 11.0 g).

Calix[4]arene 5a & 5b AKA D-D Isomeric Mixture:

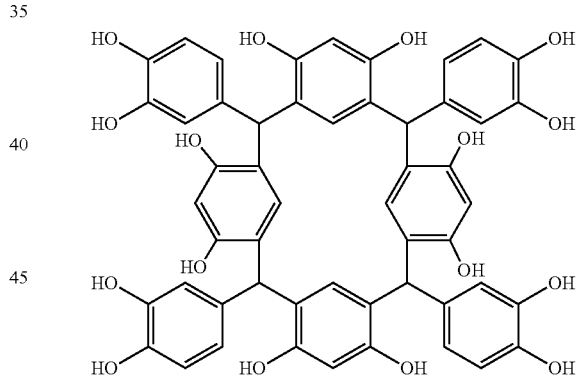

Resorcinol (7.97 g, 72.5 mmol, 1.00 equiv.) and 3,4-dihydroxybenzaldehyde (10.0 g, 72.5 mmol, 1.00 equiv.) were dissolved in a mixture of EtOH, $H_2O$ and concentrated HCl solution (3:1:1, 275 mL). The mixture was then stirred at 50° C. for 20 h. The mixture was allowed to cool to 4° C. before it was centrifuged and the supernatant was removed. The residue was suspended in water and centrifuged again. This process was repeated 3 more times. The residue was then lyophilized to yield a ~1:1 mixture of calix[4]arene$_a$ and calix[4]arene$_b$ as pale red powder (52%, 7.14 g).

This isomeric mixture was then further purified using a preparative LC-MS system. First, the mixture was dissolved in DMSO. Then $H_2O$ containing TFA (0.1%) was added (15:85). A stable gradient ($H_2O$/Acetonitrile, 95:5, without TFA, 30 mL/min, C18 column) resulted in good separation.

calix[4]arene 5a: M.p.=>300° C. $^1$H-NMR (400 MHz, DMSO) δ 8.32 (s, 8H), 8.18 (s, 4H), 8.01 (s, 4H), 6.47 (s, 4H), 6.42 (d, J=8.2 Hz, 4H), 6.19 (s, 4H), 6.07 (d, J=8.3 Hz, 4H), 6.01 (s, 4H), 5.39 (s, 4H). $^{13}$C-NMR (100 MHz, DMSO) δ 152.30, 143.78, 142.18, 136.64, 130.37, 121.09, 119.75, 117.02, 114.68, 101.95, 40.43. FTIR v. ESI-TOF calcd for $C_{52}H_{39}O_{16}$ (100%, [M]$^-$): 919.2244; found 919.2230T$_r$ ($H_2O$:AcCN, 95:5, 0.1% TFA, C18, 1 mL/min): 6.83 min.

calix[4]arene 5b: M.p.=>300° C. $^1$H-NMR (400 MHz, DMSO) δ 8.31 (s, 8H), 8.14 (s, 4H), 7.91 (s, 4H), 6.33-6.13 (m, 8H), 6.07 (s, 8H), 5.81 (d, J=8.2 Hz, 4H), 5.35 (s, 4H). $^{13}$C-NMR (100 MHz, DMSO) δ 152.59, 143.60, 142.02, 135.63, 132.00, 128.84, 121.62, 120.86, 120.01, 116.81, 114.51, 101.91, 101.73, 41.19. HRMS ESI-TOF calcd for $C_{52}H_{39}O_{16}$ (100%, [M]$^-$): 919.2244; found 919.2227. T$_r$ ($H_2O$:AcCN, 95:5, 0.1% TFA, C18, 1 mL/min): 8.92 min.

Coating Compositions and Stability Assays. A macrocyclic compound (1 mg/mL) was dissolved in DMSO. To this solution was added to 10 mM to 1.5 M salts in aqueous buffer (pH 4-10). Various substrates were coated by dipping the substrates in the coating mixture (e.g., see FIGS. 12-16) and the stability of the coating compositions were tested by incubating the coated substrates in PBS at 36° C. overnight (e.g., see FIG. 7-16). It was found that varying the components, pH, and buffers all had an effect on the stability of the coatings. For example, 1 mg/mL of the arene were dissolved in DMSO (10 volume % of the total coating solution). To this solution the buffered aqueous solution containing the salt of choice and the buffer (90% of total coating solution) was added. Then the pH was adjusted using HCl or NaOH solutions. The solution was transferred to a glass vial and the different substrates where added. The vial was sealed and placed on a rocking platform for 24 h. The substrate was rinsed with DI $H_2O$ then dried with a $N_2$ flow. Buffers used included $Na_2CO_3$ (pH 11), bicine (ph 8-9), bis-tris (pH 6-7), tris (pH 7), sodium acetate (pH 4-5). The Buffer concentration used were between 0.1 and 2.2 M. Salt concentration used were between 0 and 1.5 M.

Drug Surrogate Assay: Planar samples of PDMS were prepared by casting Sylgard 84 (Dow Corning) in a 10:1 ratio on a silanized silicon wafers (100) for ease of release. After curing at 90 C for 2 hours, the PDMS was removed and cut into small samples. For the coated samples, the planar side was then exposed to coated solution overnight, rinsed with DI water, and dried with $N_2$ gas. Samples were then placed in separate baths of 100 μM Rhodamine B solution for 3 hours and imaged using confocal z-stacks (Zeiss 710 Axio-Observer) with a step size of 3.65 μm from the surface into the sample. The absorbance profile was then created using ImageJ software to plot Z-axis profiles of the z-stacks. Graphpad Prism software was used to find the area under the Z-axis profiles for comparison.

Sessile Contact Angle: 2 μL drops were placed on planar samples prepared as in the previous section. Contact angles were measured using Ramé-Hart DropImage analysis software and hardware setup.

Preliminary Cell Toxicity Assay: PDMS surfaces were prepared by pouring Sylgard 84 (10:1) into tissue culture polystyrene 12 wells and curing for 2 hours at 90 C. The plates were then sterilized by exposure to UV light for 30 minutes. After sterilization NIH 3T3 fibroblasts were seeded at a density of 5000 cells/cm$^3$ in Dulbecco's Modified Eagle Medium (DMEM) with 10% fetal bovine serum and 1% Pen/Strep. After 3 days of growth at 37 C, 5% oxygen, cells were stained using a solution of 2 μM Calcein® (Life Technologies). Because this assay was done in an open system, dead cells were not stained.

Mass Spectroscopy. Standard mass spectroscopy protocols can be used to study the macrocycles produced by methods described herein, including those presented in Kiremire et al. "Mass Spectrometry of Macrocyclic Compounds" *Rapid Communications in Mass Spectrometry* 5(11):543-556 (1991) and the publications cited above.

HPLC. Standard HPLC protocols can be used to study the macrocycles produced by methods described herein, including those presented in the publications cited above.

NMR. Standard NMR protocols can be used to study the macrocycles produced by methods described herein, including those presented in the publications cited above.

Testing the Coating Composition versus Pyrogallol and Lignin on a PDMS Surface. It was found that when the coating compositions disclosed herein were compared against similar coating materials (pyrogallol, and lignin), the coating compositions of the disclosure had the greatest effect in increasing the wettability of a PDMS surface (e.g., see FIG. 22). It was further found that the coating compositions disclosed herein were more effective in preventing the adsorption of a hydrophobic drug surrogate, Rhodamine B, by PDMS than pyrogallol, and lignin (e.g., see FIG. 22). Further, in cell culture experiments it was found that coating compositions of the disclosure showed increased adherence in comparison to PDMS alone and further no markers of toxicity were detected (e.g., see FIG. 22).

Example 2

$C_1$-BODIPY-$C_{12}$ (4,4-Difluoro-5-Methyl-4-Bora-3a,4a-Diaza-s-Indacene-3-Dodecanoic Acid), purchased from Thermofisher (Cat No. D3823), is a BODIPY labeled fatty acid analog. Planar samples were incubated for 3 hours at room temperature in solutions of 1 μM $C_1$-BODIPY-$C_{12}$ with 0.25% bovine albumin serum. Imaging and analysis were made. Perkin Elmer Informatics, Inc's ChemDraw software calculated cLogP for each molecule for direct comparison.

As demonstrated the ability of the Arenes of the disclosure were shown to block Rhodamine B absorption around 90%. In this example, the Arene's ability to also block a fatty acid analog ($C_1$-BODIPY-$C_{12}$) with a very high calculated Log P of ~7 was analyzed. The Arene coating blocked 95% of the absorption of $C_1$-BODIPY-$C_{12}$, demonstrating its ability to perform as an effective barrier to a diverse set of small molecules (see, FIG. 23).

Example 3

Blank flouro-silanized 4 inch wafers were mounted in acrylic ring molds. 5 g of mixed and degassed Sylgard 184 mixed 10:1 was poured onto the wafers on a level surface and allowed to spread at room temperature for 30 minutes. Coated wafers were then cured at 90° C. for 2 hours and subsequently de-molded. Uncut planar sides were coated with arene. MOCON, Inc. performed oxygen flux measurements using ASTM F1927 standard with the modification of using the OxTran 210 sensor in order to reach higher oxygen flux readings as necessary. Samples were masked down to 5 cm². Thickness measurements were performed using a digital thickness gage (Mitutoyo 547-520S). Two samples of each condition were tested for each set, with two sets measured by two different operators. To determine statistical significance, parametric t-tests were performed with a confidence level of 95% using Prism statistical software by Graphpad.

Oxygen diffusion through PDMS for microphysiological systems is important for long-term viability of cells and is one of the many attributes that researchers choose PDMS for many of these systems currently in use. In development of methods to block small molecule absorption, glass like coatings are effective barriers for small molecules, but also oxygen, a major hurdle to using these barrier coatings for cell culture devices. An effective way of measuring the change in oxygen diffusion caused by a barrier coating is to perform an oxygen flux measurement to calculate permeability.

Permeability (P) values were calculated using the Oxygen Transmission Rate (OTR) and film thickness (t) according to the following equation:

$$P = OTR \times t$$

Uncoated and Arene coated PDMS samples (N=4) demonstrated oxygen permeabilities of 1.335e+006 and 1.309e+006 cc*mil/[m2 day], respectively. The p-value of parametric t-tests was 0.56 demonstrating no significant difference between oxygen diffusion in uncoated and Arene-coated samples, therefore preserving the ease of oxygen transport through the device. (See, FIG. 24).

A number of embodiments have been described herein. Nevertheless, it will be understood that various modifications may be made without departing from the spirit and scope of this disclosure. Accordingly, other embodiments are within the scope of the following claims.

What is claimed is:

1. A coating composition comprising one or more salts selected from MgCl₂, CaCl₂ and combination thereof, and one or more macrocycles in a bicine buffer, wherein the one or more macrocycles comprise the structure:

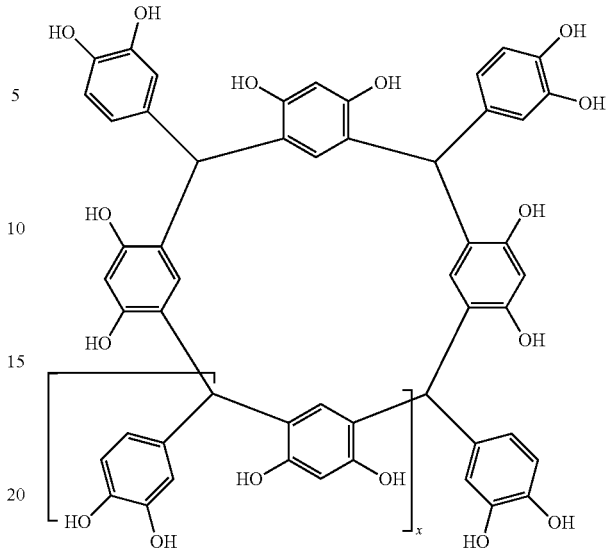

wherein,
x is an integer selected from 1, 2, 3, and 4, or a range including any two of the foregoing integers.

2. The coating composition of claim 1, wherein the composition comprises between 0.5 mg/mL and 5 mg/mL of the one or more macrocycles.

3. The coating composition of claim 2, wherein the composition comprises 1 mg/mL of the one or more macrocycles.

4. The coating composition of claim 1, wherein the one or more macrocycles is dissolved in polar aprotic solvent.

5. The coating composition of claim 1, wherein the one or more salts is used at a concentration of 0.1M to 3.0M.

6. The coating composition of claim 1, wherein the pH of the aqueous buffer is from pH 7 to pH 10.

7. A method of coating one or more surfaces of a substrate comprising coating the substrate with the coating composition of claim 1.

8. The method of claim 7, wherein the one or more surfaces of the substrate is coated with the coating composition using dip coating or spin coating.

9. The method of claim 7, wherein the one or more surfaces of the substrate comprises a polymer material.

10. The method of claim 9, wherein the polymer material is a synthetic polymer material.

11. The method of claim 10, wherein the synthetic polymer material is poly(dimethyl siloxane) (PDMS).

12. The method of claim 7, wherein one of more surfaces that of a microfluidic or microphysiological system (MPS) are coated with the coating composition.

13. A microfluidic or MPS comprising one or more surfaces coated with the coating composition of claim 1.

14. The microfluidic or MPS of claim 13, wherein the microfluidic or MPS comprises PDMS.

* * * * *